(12) United States Patent
Schneider et al.

(10) Patent No.: US 9,775,749 B2
(45) Date of Patent: Oct. 3, 2017

(54) APPARATUSES AND METHODS FOR TRANSFERRING AND BONDING SUBSTRATES

(71) Applicant: The Procter & Gamble Company, Cincinnati, OH (US)

(72) Inventors: Uwe Schneider, Cincinnati, OH (US); Michael Devin Long, Springfield Township, OH (US); David C. Ordway, Oxford, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/005,413

(22) Filed: Jan. 25, 2016

(65) Prior Publication Data

US 2016/0220424 A1    Aug. 4, 2016

Related U.S. Application Data

(60) Provisional application No. 62/111,750, filed on Feb. 4, 2015.

(51) Int. Cl.
*B29C 65/00* (2006.01)
*A61F 13/15* (2006.01)

(52) U.S. Cl.
CPC .. *A61F 13/15699* (2013.01); *A61F 13/15723* (2013.01); *A61F 13/15739* (2013.01);
(Continued)

(58) Field of Classification Search
CPC .......... A61F 13/15699; A61F 13/15739; A61F 13/15764; A61F 13/15804;
(Continued)

(56) References Cited

U.S. PATENT DOCUMENTS 2,957,639 A * 10/1960 Muller ................... B65H 23/14
                                                          242/419.9
3,622,421 A * 11/1971 Cook ........................ B26F 3/06
                                                          156/290
(Continued)

FOREIGN PATENT DOCUMENTS

EP          0 844 062 A1     5/1998

OTHER PUBLICATIONS

PCT International Search Report, dated May 20, 2016, 9 pages.
(Continued)

*Primary Examiner* — John Goff
(74) *Attorney, Agent, or Firm* — Sarah M. DeCristofaro

(57) ABSTRACT

A method for mechanically deforming, such as by bonding, a substrate assembly. The substrate assembly may be advanced at first velocity toward a bonder apparatus. The bonder apparatus may rotate at a second velocity, which is less than or equal to the first velocity. The bonder apparatus may include a support surface and a process assembly. The substrate assembly may be contracted prior to advancing onto the bonder apparatus. A first process assembly may receive a leading portion of the substrate assembly and a subsequent process assembly may receive a trailing portion. The leading portion and the trailing portion define a product arc length, which is less than or equal to a process product pitch. One or more processes may be performed on the substrate assembly. The substrate assembly may then be removed from the apparatus and advanced through a metering assembly such that the substrate assembly exits at the first velocity and may be expanded such that the leading portion and the trailing portion are separated by the process product pitch.

19 Claims, 13 Drawing Sheets

(52) U.S. Cl.
CPC .. *A61F 13/15764* (2013.01); *A61F 13/15804* (2013.01); *A61F 2013/15861* (2013.01)

(58) Field of Classification Search
CPC .. A61F 2013/15861; A61F 2013/15869; A61F 2013/15878; A61F 2013/15886; A61F 2013/15902; A61F 2013/1591; A61F 2013/15829; B29C 65/7847; B29C 65/7882; B29C 65/7885; B29C 66/3432; B29C 66/343; B29C 66/83411
USPC .............. 156/160, 163, 164, 229, 324
See application file for complete search history.

(56) References Cited

U.S. PATENT DOCUMENTS

| | | | |
|---|---|---|---|
| 3,860,003 A | 1/1975 | Buell | |
| 3,896,808 A * | 7/1975 | Szpur | A61M 35/006 15/244.1 |
| 4,089,729 A * | 5/1978 | Leloux | B29C 65/18 156/498 |
| 4,606,970 A * | 8/1986 | Sharps, Jr. | B32B 27/12 383/116 |
| 4,610,678 A | 9/1986 | Weisman et al. | |
| 4,673,402 A | 6/1987 | Weisman et al. | |
| 4,695,278 A | 9/1987 | Lawson | |
| 4,704,115 A | 11/1987 | Buell | |
| 4,795,454 A | 1/1989 | Dragoo | |
| 4,834,735 A | 5/1989 | Alemany et al. | |
| 4,888,231 A | 12/1989 | Angstadt | |
| 4,909,803 A | 3/1990 | Aziz et al. | |
| 5,562,646 A | 10/1996 | Goldman et al. | |
| 5,599,335 A | 2/1997 | Goldman et al. | |
| 5,628,097 A | 5/1997 | Benson et al. | |
| 5,669,894 A | 9/1997 | Goldman et al. | |
| 5,916,661 A | 6/1999 | Benson et al. | |
| 6,107,539 A | 8/2000 | Palumbo et al. | |
| 6,248,195 B1 | 6/2001 | Schmitz | |
| 6,471,804 B1 * | 10/2002 | Tennby | A61F 13/15699 156/256 |
| 6,545,197 B1 | 4/2003 | Muller et al. | |
| 6,790,798 B1 | 9/2004 | Suzuki et al. | |
| 7,569,039 B2 | 8/2009 | Matsuda et al. | |
| 7,587,966 B2 | 9/2009 | Nakakado et al. | |
| 8,778,127 B2 | 7/2014 | Schneider et al. | |
| 2004/0097895 A1 | 5/2004 | Busam et al. | |
| 2004/0158212 A1 | 8/2004 | Ponomarenko et al. | |
| 2005/0107764 A1 | 5/2005 | Matsuda et al. | |
| 2009/0312730 A1 | 12/2009 | LaVon et al. | |
| 2012/0061015 A1 | 3/2012 | LaVon et al. | |
| 2012/0061016 A1 | 3/2012 | LaVon et al. | |
| 2013/0213547 A1 * | 8/2013 | Schneider | A61F 13/4963 156/60 |
| 2013/0218116 A1 | 8/2013 | Schneider et al. | |
| 2013/0255861 A1 | 10/2013 | Schneider | |
| 2013/0255862 A1 | 10/2013 | Schneider et al. | |
| 2013/0255863 A1 | 10/2013 | LaVon et al. | |
| 2013/0255864 A1 | 10/2013 | Schneider et al. | |
| 2013/0255865 A1 | 10/2013 | Brown et al. | |
| 2014/0000798 A1 | 1/2014 | Hargett et al. | |
| 2014/0110053 A1 | 4/2014 | Ordway et al. | |
| 2014/0305593 A1 | 10/2014 | Schneider et al. | |
| 2015/0202727 A1 | 7/2015 | Yamamoto et al. | |

OTHER PUBLICATIONS

PCT International Search Report, dated May 4, 2016, 10 pages.
U.S. Appl. No. 15/005,381, filed Jan. 25, 2016, Schneider, et al.
U.S. Appl. No. 15/005,398, filed Jan. 25, 2016, Schneider, et al.

* cited by examiner

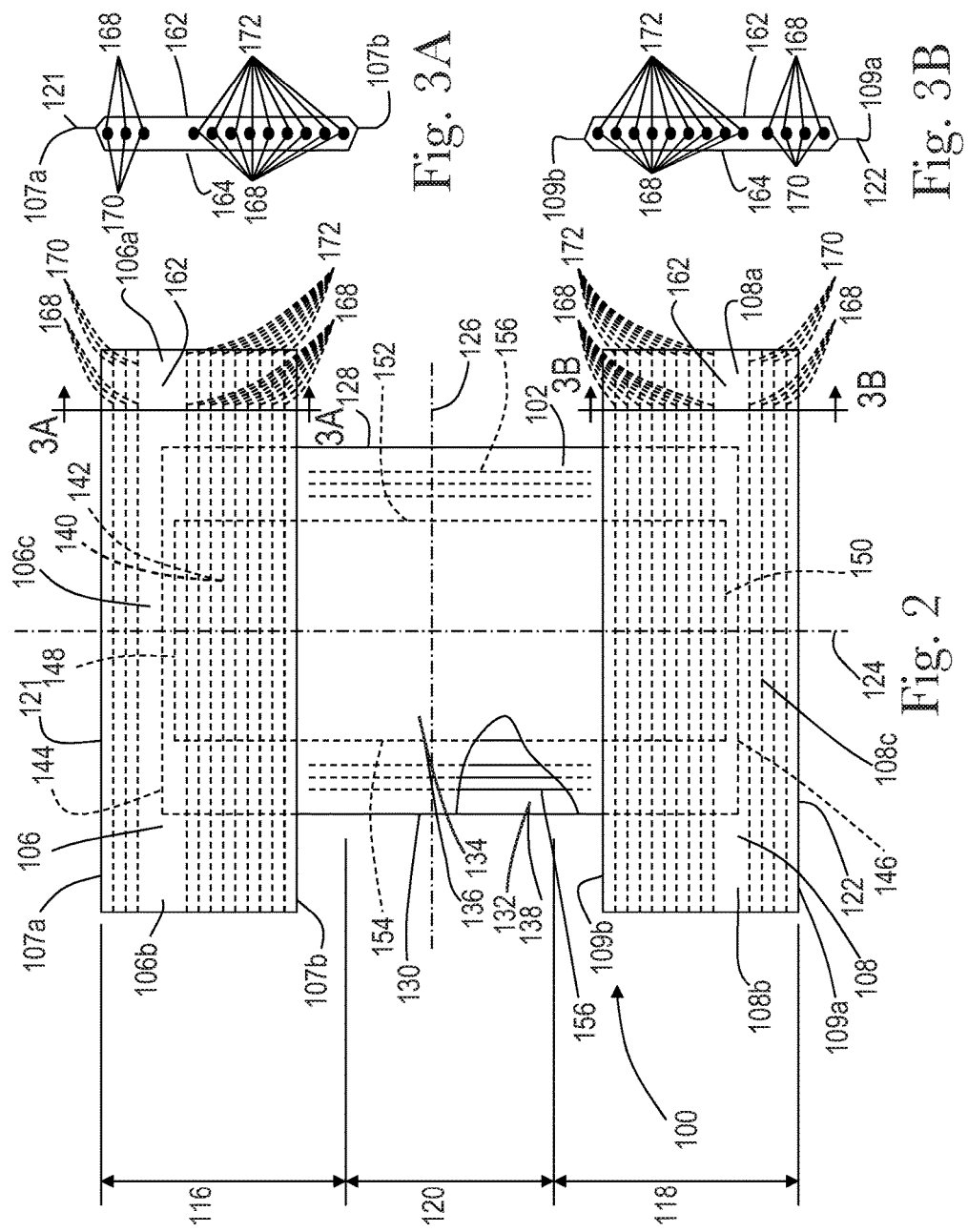

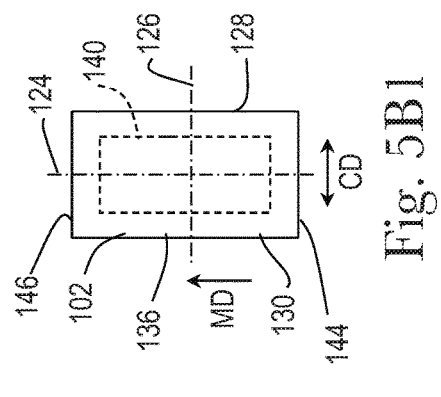
Fig. 5B1
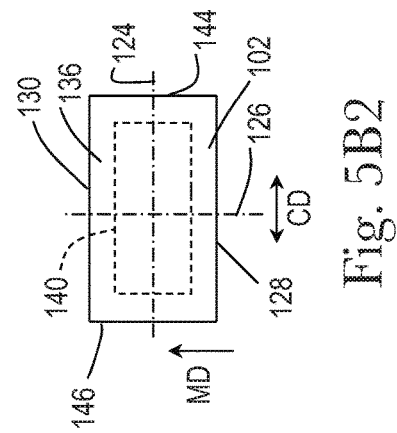
Fig. 5B2
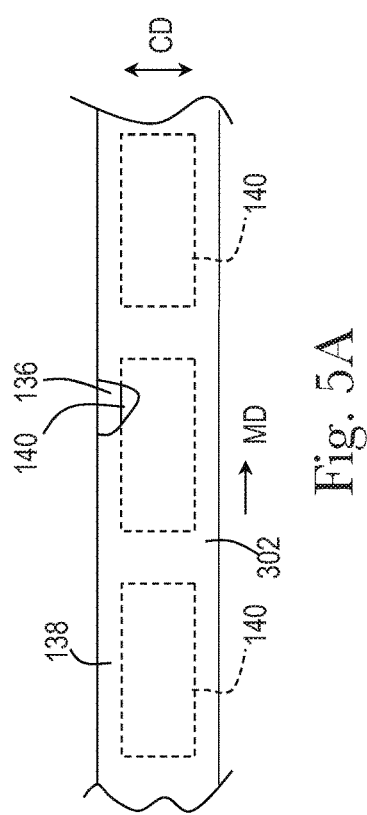
Fig. 5A
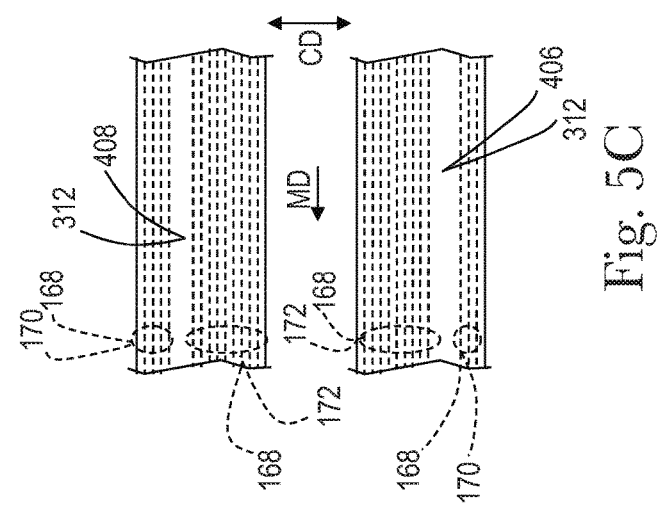
Fig. 5C

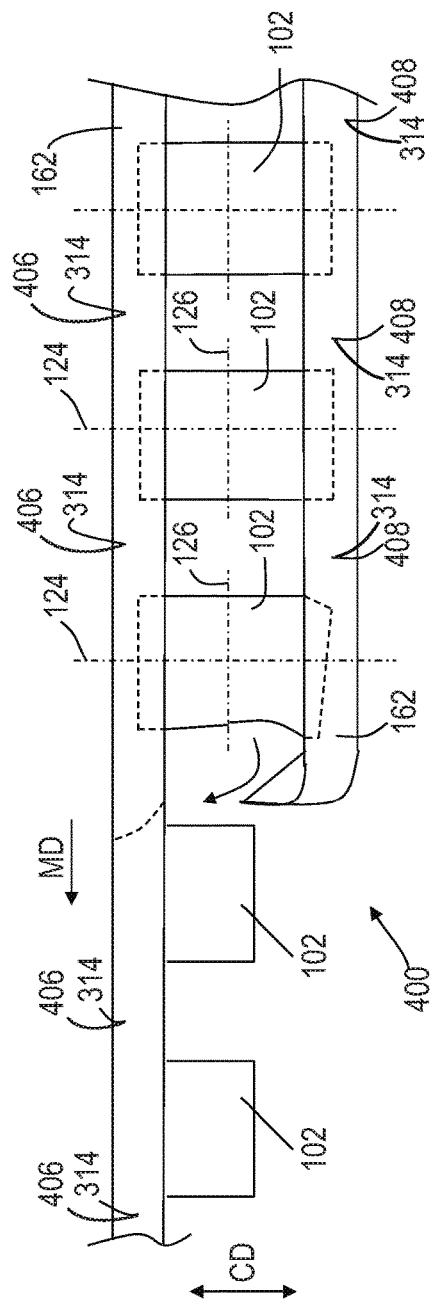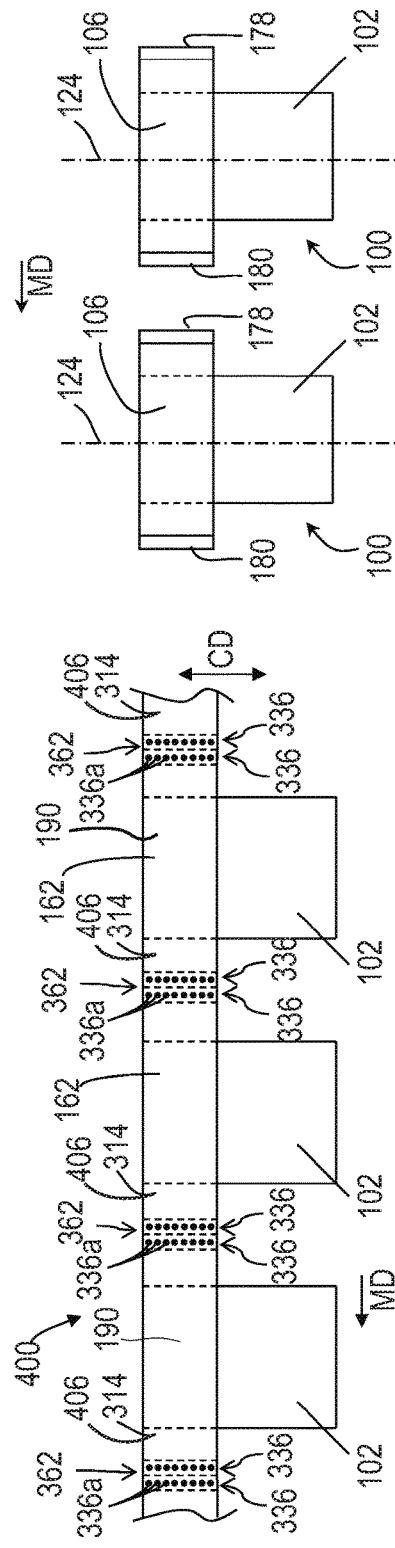

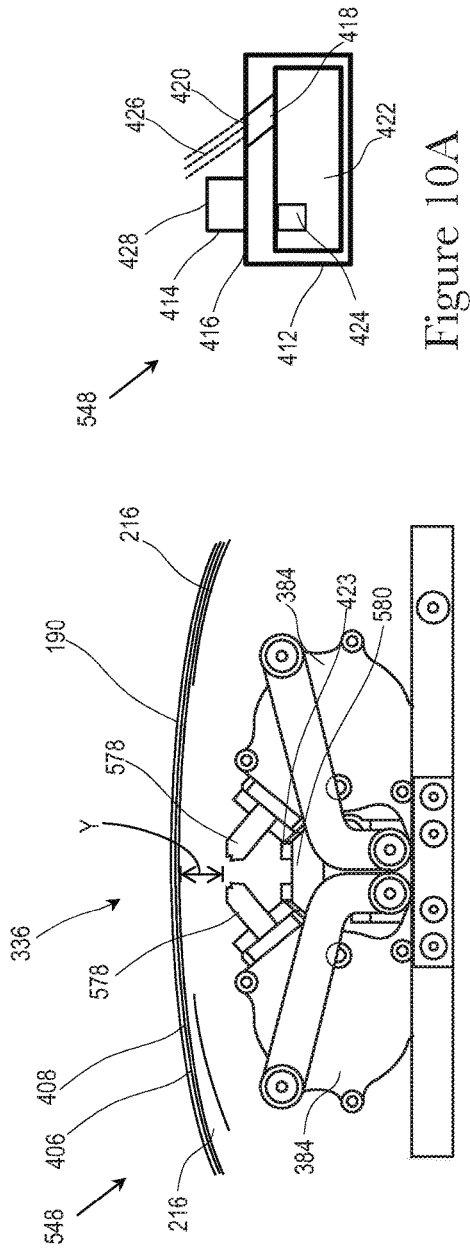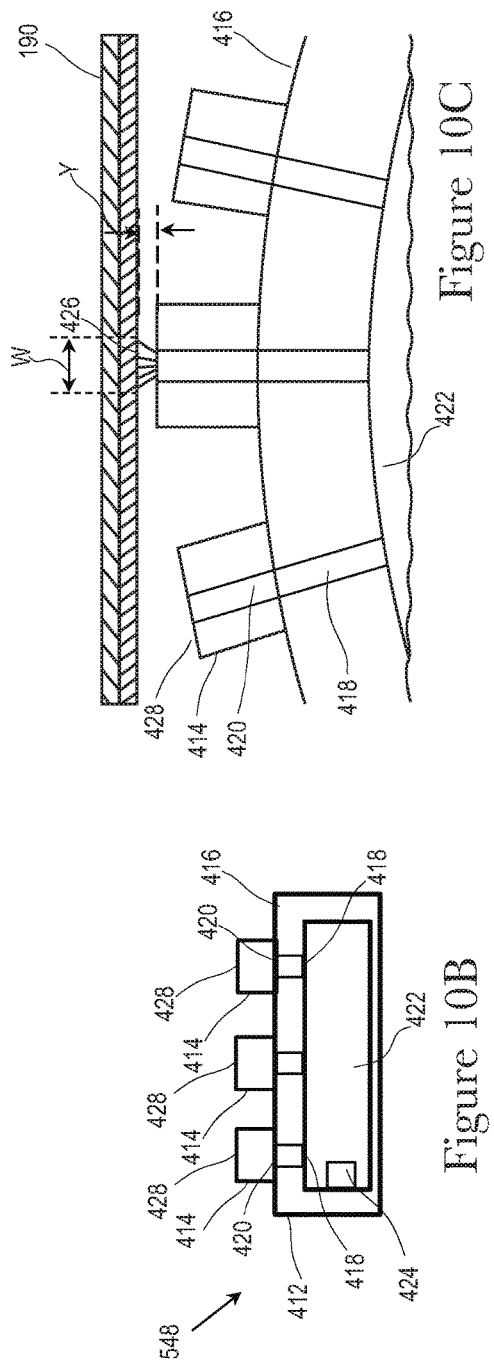

APPARATUSES AND METHODS FOR TRANSFERRING AND BONDING SUBSTRATES

CROSS REFERENCE TO RELATED APPLICATIONS

This application claims the benefit of U.S. Provisional Application No. 62/111,750 filed on Feb. 4, 2015, which is herein incorporated herein by reference.

TECHNICAL FIELD

The present disclosure relates to methods for manufacturing absorbent articles, and more particularly, to apparatuses and methods for bonding two or more partially meltable materials.

BACKGROUND

Disposable absorbent articles, in particular, disposable diapers, are designed to be worn by people experiencing incontinence, including infants and invalids. Such diapers are worn about the lower torso of the wearer and are intended to absorb and contain urine and other bodily discharges, thus preventing the soiling, wetting, or similar contamination of articles that may come into contact with a diaper during use (e.g., clothing, bedding, other people, etc.). Disposable diapers are available in the form of pull-on diapers, also referred to as training pants, having fixed sides, or taped diapers having unfixed sides.

Along an assembly line, various types of articles, such as diapers and other absorbent articles, may be assembled by adding components to and/or otherwise modifying an advancing, continuous web of material. In some processes, advancing webs of material are combined with other advancing webs of material. In other processes, individual components created from advancing webs of material are combined with advancing webs of material, which in turn, are then combined with other advancing webs of material. In some cases, individual components created from advancing web or webs are combined with other individual components created from other advancing web or webs. Webs of material and component parts used to manufacture diapers may include: backsheets, topsheets, leg cuffs, waist bands, absorbent core components, front and/or back ears, fastening components, and various types of elastic webs and components such as leg elastics, barrier leg cuff elastics, stretch side panels, and waist elastics. Once the desired component parts are assembled, the advancing web(s) and component parts are subjected to a final knife cut to separate the web(s) into discrete diapers or other absorbent articles.

In some converting configurations, discrete chassis spaced apart from each other are advanced in a machine direction and are arranged with a longitudinal axis parallel with the cross direction. Opposing waist regions of discrete chassis are then connected with continuous lengths of elastically extendable front and back belt webs advancing in the machine direction. While connected with the chassis, the front and back belt webs are maintained in a fully stretched condition along the machine direction, forming a continuous length of absorbent articles. The continuous length of absorbent articles may then be folded in a cross direction. During the folding process in some converting configurations, one of the front and back belt webs is folded into a facing relationship with the opposing belt. The front and back belts may then be bonded together to create the side seams on diapers.

Diapers come in a variety of sizes. Thus, one diaper may include a larger chassis and a larger belt as compared to another diaper which may include a smaller chassis and a smaller belt. The manufacturing process for these absorbent articles is desired to be such that the diaper including the larger chassis and the larger belt can be manufactured on the same equipment or similar equipment as the diaper including the smaller chassis and the smaller belt. Having to switch out equipment or to make large modifications to the equipment for manufacturing different sized articles is costly and time consuming for manufacturers.

Thus, it would be beneficial to provide an apparatus and a method for transferring and bonding absorbent articles of different sizes.

SUMMARY

Aspects of the present disclosure involve apparatuses and methods for manufacturing absorbent articles, and more particularly, methods for mechanically deforming substrates during the manufacture of disposable absorbent articles. Particular embodiments of methods of manufacture disclosed herein provide for forming side seams in various types of diaper configurations. While the present disclosure relates mainly to forming side seams in diaper pants, it is to be appreciated that the methods and apparatuses disclosed herein can also be applied to other mechanical deformation used on diapers as well as other types of absorbent articles.

In one embodiment, a method for transferring and bonding includes the steps of: advancing a substrate assembly in a machine direction at a first velocity, wherein the substrate assembly comprises a process product pitch defined by a leading portion and a trailing portion, and wherein the substrate assembly comprises a first substrate in facing relationship with a second substrate; rotating a bonder apparatus about an axis of rotation at a second velocity, wherein the bonder apparatus comprises a support surface and a process assembly disposed on a portion of the support surface, and wherein the first velocity is greater than the second velocity; contracting the substrate assembly; receiving the leading portion on the process assembly; receiving the trailing portion on a subsequent process assembly, wherein the leading portion and the trailing portion define a product arc length, and wherein the product arc length is less than or equal to the process product pitch; seaming the leading portion and the trailing portion of the substrate assembly; removing the substrate assembly from the support surface and the process assembly; advancing the substrate assembly through an exit metering assembly such that the substrate assembly exits the metering assembly at the first velocity; and expanding the substrate assembly such that the leading portion and the trailing portion are separated by the process product pitch.

In another embodiment, a method for forming a bond, the method comprising the steps of: advancing a substrate assembly in a machine direction at a first velocity, wherein the substrate assembly comprises a process product pitch defined by a leading portion and a trailing portion; moving a bonder apparatus at a second velocity, wherein the bonder apparatus comprises a support surface and a process assembly disposed on a portion of the support surface, and wherein the first velocity is greater than or equal to the second velocity; advancing the substrate assembly to a first metering roll, wherein the first metering roll is configured to rotate about an axis of rotation at the first velocity; contracting the substrate assembly; receiving the substrate assembly on the bonder apparatus, wherein the leading portion is disposed on the process assembly and the trailing portion is disposed on a subsequent process assembly and the portion of the substrate assembly between the leading portion and the trailing portion is disposed on the support surface; advancing the substrate assembly on the bonder apparatus at the second velocity; seaming a portion of the leading portion and a portion of the trailing portion of the substrate assembly; bonding at least a portion of the leading portion and bonding at least a portion of the trailing portion; removing the substrate assembly from the support surface and the process assembly; advancing the substrate assembly through an exit metering assembly such that the substrate assembly exits the metering assembly at the first velocity; and expanding the substrate assembly such that the leading portion and the trailing portion are separated by the process product pitch.

In another embodiment, a method for forming a bond, the method comprising the steps of: advancing a substrate assembly in a machine direction at a first velocity, wherein the substrate assembly comprises a process product pitch defined by a leading portion and a trailing portion, and wherein the substrate assembly comprises a first substrate in facing relationship with a second substrate; advancing the substrate assembly through a first metering assembly, wherein the first metering assembly comprises a first roll and a second roll each configured to rotate at the first velocity; providing a bonder apparatus comprising a first transition apparatus and a second transition apparatus adjacent the first transition apparatus, wherein the first transition apparatus comprises a first conveyor and the second transition apparatus comprises a second conveyor, and wherein the first conveyor and the second conveyor define an entry region and an exit region opposite the entry region; advancing the first conveyor and the second conveyor at a second velocity, wherein the first velocity is greater than or equal to the second velocity; contracting the substrate assembly; advancing the substrate assembly through the entry region and between the first conveyor and the second conveyor at the second velocity; engaging the substrate assembly and a process assembly to mechanically deform at least a portion of the substrate assembly; advancing the substrate assembly through the exit region of the bonder apparatus at the second velocity; compressing at least a portion of the substrate assembly; advancing the substrate assembly through a second metering assembly such that the substrate assembly exits the second metering assembly at the first velocity; and expanding the substrate assembly such that the leading portion and the trailing portion are separated by the process product pitch.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIG. 2 is a partially cut away plan view of the diaper pant shown in FIG. 1;

FIG. 3A is a cross-sectional view of the diaper pant of FIG. 2 taken along line 3A-3A of FIG. 2;
FIG. 3B is a cross-sectional view of the diaper pant of FIG. 2 taken along line 3B-3B of FIG. 2;
FIG. 5A is a top view of a chassis assembly taken along line 5A-5A of FIG. 4 in accordance with one non-limiting embodiment of the present disclosure;
FIG. 5B1 is a top view of a discrete chassis taken along line 5B1-5B1 of FIG. 4 in accordance with one non-limiting embodiment of the present disclosure;
FIG. 5B2 is a top view of a discrete chassis taken along line 5B2-5B2 of FIG. 4 in accordance with one non-limiting embodiment of the present disclosure;
FIG. 5C is a top view of elastic belt substrates taken along line 5C-5C of FIG. 4 in accordance with one non-limiting embodiment of the present disclosure;
FIG. 5D is a top view of multiple discrete chassis attached to a first elastic belt substrate and a second elastic belt substrate taken along line 5D-5D of FIG. 4 in accordance with one non-limiting embodiment of the present disclosure;
FIG. 5E is a top view of multiple discrete chassis attached to a substrate assembly taken along line 5E-5E of FIG. 4 in accordance with one non-limiting embodiment of the present disclosure;
FIG. 5F is a top view of two discrete absorbent articles taken along line 5F-5F of FIG. 4 in accordance with one non-limiting embodiment of the present disclosure;
FIG. 9 is a side view of a seaming station in accordance with one non-limiting embodiment of the present disclosure;
FIG. 10A is a side view of a seaming station in accordance with one non-limiting embodiment of the present disclosure;
FIG. 10B is a side view of a seaming station in accordance with one non-limiting embodiment of the present disclosure;
FIG. 10C is a partial side view of a seaming station in accordance with one non-limiting embodiment of the present disclosure.

DETAILED DESCRIPTION

Figure 1:
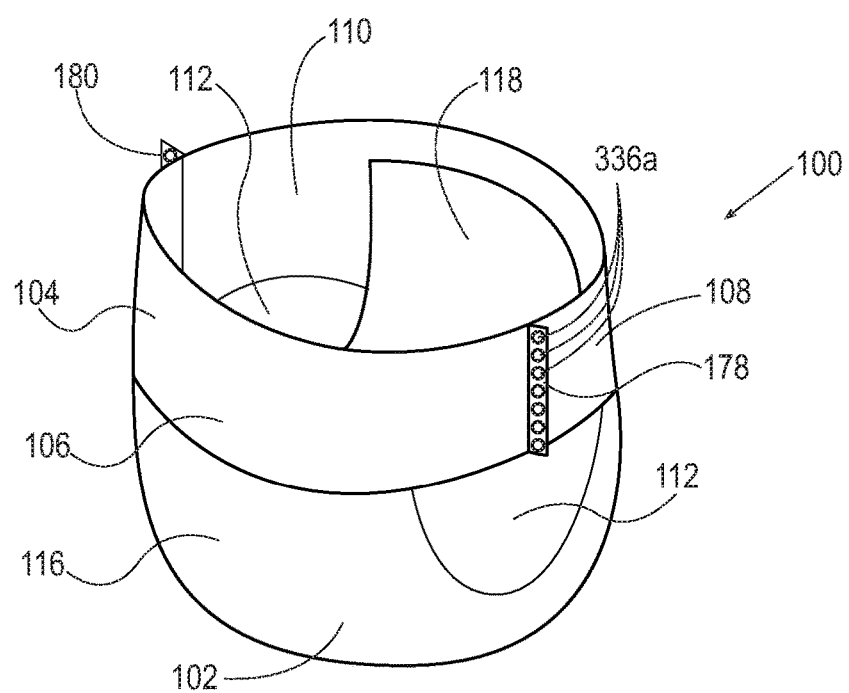
FIG. 1 is a perspective view of a diaper pant.

The methods and apparatuses described herein relate to transferring and processing substrates. For example, a substrate assembly may be transferred and may undergo a bonding process. More specifically, as the substrate assembly is being transferred, portions of substrates may be overlapped and a jet of heated fluid may be delivered from an orifice to at least partially melt the overlapping substrate portions. The jet of heated fluid may penetrate the substrate portions and at least partially melt the overlapping substrate portions where the substrate portions interface at an overlap area. The location of the substrate portions relative to the orifice may be controlled such that the substrate portions are held at a predetermined distance away from the orifice during the heating operation. Pressure may then be applied at the overlap area thereby joining the substrate portions together. In all the embodiments described herein, the fluid may include ambient air or other gases.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

As used herein, the term "joining" describes a configuration whereby a first element is directly secured to another element by affixing the first element directly to the other element.

As used herein, the term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a substrate, layer or layers or fibrous materials, nonwovens, films and foils such as polymeric films or metallic foils. These materials may be used alone or may comprise two or more layers laminated together. As such, a web is a substrate.

As used herein, the term "pull-on diaper" refers to a garment that is generally worn by infants and sufferers of incontinence, which is pulled on like pants. It should be understood, however, that the present disclosure is also applicable to other absorbent articles, such as taped diapers, incontinence briefs, feminine hygiene garments, and the like, including absorbent articles intended for use by infants, children, and adults.

As used herein, the term "at least partially melted" refers to materials at least a portion of which have reached at least a softening point temperature, but have not reached a melt point temperature. "Melted" also refers, in its ordinary sense, to materials which have exceeded their melt point temperatures over at least a portion of the material. "Meltable" refers to materials that at least soften when heated or when some other energy is applied or generated.

The present disclosure relates to methods and apparatuses for bonding substrates together. As discussed in more detail below, the bonder apparatus is rotated about an axis of rotation and a substrate assembly may be advanced in a machine direction and received on the bonder apparatus. The bonder apparatus may adjust the velocity of the substrate assembly prior to bonding. A portion of the substrate assembly may undergo bonding by a seaming station as the substrate assembly continues to rotate with the bonder apparatus. Further, in some embodiments, the substrate assembly may be compressed.

As discussed below, the bonder apparatus may be configured to partially melt and/or compress the substrates while traveling on the bonder apparatus to minimize deformation of weak, partially melted substrates as the substrates advance in the machine direction MD. More specifically, a fluid is heated to a temperature sufficient to at least partially melt a portion of the substrate assembly. As the bonder apparatus rotates, the fluid nozzle moves radially outward toward the aperture in the receiving surface of the apparatus. The fluid nozzle directs a jet of the heated fluid through the aperture and onto an area of the substrate assembly, which partially melts the area. As the bonder apparatus continues to rotate, the fluid nozzle retracts radially inward from the aperture, and the press member moves radially outward. The partially melted area is then compressed between a press member and an anvil roll or anvil block, creating a discrete bond region or seam. The bonder apparatus continues to rotate and the press member retracts radially inward from the aperture. In some embodiments, the operative connection between the fluid nozzle and the press member may be configured to partially melt and compress the substrates at the same relative location in order to create a bond.

As described in greater detail below, a seam may be formed between at least two substrate layers, each substrate layer comprising one or more meltable components. A seam may also be formed between portions of the same substrate that is, for example, folded along a fold line formed between two substrate portions. The substrate portions to be bonded may be positioned adjacent one another.

It is to be appreciated that although the transfer and bonding methods and apparatuses herein may be configured to bond various types of substrates, the methods and apparatuses herein are discussed below in the context of manufacturing absorbent articles. In particular, the methods and apparatuses are discussed in the context of bonding substrates, such as belts, together to form side seams of advancing, continuous lengths of absorbent articles during production. As discussed below, an advancing continuous length of absorbent articles may include a plurality of chassis connected with a continuous first substrate and a continuous second substrate.

The continuous first and second substrates may be separated from each other along a cross direction while advancing along a machine direction MD. Each chassis may extend in the cross direction CD and may include opposing first and second end regions separated by a central region, wherein the first end regions are connected with the first substrate and the second end regions are connected with the second substrate. The chassis may also be spaced from each other along the machine direction MD. A folding apparatus operates to fold the chassis around the folding axis along the central regions and to bring the second substrate and second end region of the chassis into a facing relationship with the first substrate and first end region of the chassis. The first substrate and the second substrate in a facing relationship form a substrate assembly. The substrate assembly and the folded chassis advance in the machine direction onto the bonder apparatus such as described above.

The methods and apparatuses discussed herein may be used to bond various types of substrate configurations, some of which may be used in the manufacture of different types of absorbent articles. To help provide additional context to the subsequent discussion of the process embodiments, the following provides a general description of absorbent articles in the form of diapers that include components that may be bonded in accordance with the methods and apparatuses disclosed herein.

FIGS. 1 and 2 show an example of a diaper pant 100 that may be transferred and/or bonded with the apparatuses and methods disclosed herein. In particular, FIG. 1 shows a perspective view of a diaper pant 100 in a pre-fastened configuration, and FIG. 2 shows a plan view of the diaper pant 100 with the portion of the diaper that faces away from a wearer oriented towards the viewer. The diaper pant 100 shown in FIGS. 1 and 2 includes a chassis 102 and a ring-like elastic belt 104. As discussed below in more detail, a first elastic belt 106 and a second elastic belt 108 are connected together to form the ring-like elastic belt 104.

With continued reference to FIG. 2, the chassis 102 includes a first waist region 116, a second waist region 118, and a crotch region 119 disposed intermediate the first and second waist regions. The first waist region 116 may be configured as a front waist region, and the second waist region 118 may be configured as back waist region. In some embodiments, the length of each of the front waist region, back waist region, and crotch region 120 may be ⅓ of the length of the absorbent article 100. The diaper 100 may also include a laterally extending front waist edge 121 in the front waist region 116 and a longitudinally opposing and laterally extending back waist edge 122 in the back waist region 118. To provide a frame of reference for the present discussion, the diaper 100 and chassis 102 of FIG. 2 is shown with a longitudinal axis 124 and a lateral axis 126. In some embodiments, the longitudinal axis 124 may extend through the front waist edge 121 and through the back waist edge 122. And the lateral axis 126 may extend through a first longitudinal or right side edge 128 and through a midpoint of a second longitudinal or left side edge 130 of the chassis 102.

As shown in FIGS. 1 and 2, the diaper pant 100 may include an inner, body facing surface 132, and an outer, garment facing surface 134. The chassis 102 may include a backsheet 136 and a topsheet 138. The chassis 102 may also include an absorbent assembly 140 including an absorbent core 142 that may be disposed between a portion of the topsheet 138 and the backsheet 136. As discussed in more detail below, the diaper 100 may also include other features, such as leg elastics and/or leg cuffs to enhance the fit around the legs of the wearer.

As shown in FIG. 2, the periphery of the chassis 102 may be defined by the first longitudinal side edge 128, a second longitudinal side edge 130; a first laterally extending end edge 144 disposed in the first waist region 116; and a second laterally extending end edge 146 disposed in the second waist region 118. Both side edges 128 and 130 extend longitudinally between the first end edge 144 and the second end edge 146. As shown in FIG. 2, the laterally extending end edges 144 and 146 are located longitudinally inward from the laterally extending front waist edge 121 in the front waist region 116 and the laterally extending back waist edge 122 in the back waist region 118. When the diaper pant 100 is worn on the lower torso of a wearer, the front waist edge 121 and the back waist edge 122 of the chassis 102 may encircle a portion of the waist of the wearer. At the same time, the chassis side edges 128 and 130 may encircle at least a portion of the legs of the wearer. And the crotch region 120 may be generally positioned between the legs of the wearer with the absorbent core 142 extending from the front waist region 116 through the crotch region 120 to the back waist region 118.

It is also to be appreciated that a portion or the whole of the diaper 100 may also be made laterally extensible. The additional extensibility may help allow the diaper 100 to conform to the body of a wearer during movement by the wearer. The additional extensibility may also help, for example, allow the user of the diaper 100 including a chassis 102 having a particular size before extension to extend the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper pant 100 may include a backsheet 136. The backsheet 136 may also define the outer surface 134 of the chassis 102. The backsheet 136 may be impervious to fluids (e.g., menses, urine, and/or runny feces) and may be manufactured from a thin plastic film, although other flexible liquid impervious materials may also be used. The backsheet 136 may prevent the exudates absorbed and contained in the absorbent core from wetting articles which contact the diaper 100, such as bedsheets, pajamas, and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the diaper pant 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

As mentioned above, the diaper pant 100 may also include an absorbent assembly 140 that is joined to the chassis 102. As shown in FIG. 2, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprises primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 and 2004/0097895.

As previously mentioned, the diaper 100 may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; 4,909,803; U.S. Patent Publication No. 2009/0312730 A1; and U.S. Patent Publication No. 2013/0255865 A1.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening 110 and continuous perimeter leg openings 112 such as shown in FIG. 1. As previously mentioned, the ring-like elastic belt 104 is defined by a first elastic belt 106 connected with a second elastic belt 108. As shown in FIG. 2, the first elastic belt 106 defines first and second opposing end regions 106a, 106b and a central region 106c, and the second elastic 108 belt defines first and second opposing end regions 108a, 108b and a central region 108c.

The central region 106c of the first elastic belt is connected with the first waist region 116 of the chassis 102, and the central region 108c of the second elastic belt 108 is connected with the second waist region 118 of the chassis 102. As shown in FIG. 1, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

As shown in FIGS. 2, 3A, and 3B, the first elastic belt 106 also defines an outer lateral edge 107a and an inner lateral edge 107b, and the second elastic belt 108 defines an outer lateral edge 109a and an inner lateral edge 109b. The outer lateral edges 107a, 109a may also define the front waist edge 121 and the laterally extending back waist edge 122. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts may include a nonwoven web of synthetic fibers, and may include a stretchable nonwoven. In other embodiments, the first and second elastic belts may include an inner hydrophobic, non-stretchable nonwoven material and an outer hydrophobic, non-stretchable nonwoven material.

The first and second elastic belts 106, 108 may also each include belt elastic material interposed between the outer layer 162 and the inner layer 164. The belt elastic material may include one or more elastic elements such as strands, ribbons, or panels extending along the lengths of the elastic belts. As shown in FIGS. 2, 3A, and 3B, the belt elastic material may include a plurality of elastic strands 168 that may be referred to herein as outer, waist elastics 170 and inner, waist elastics 172.

As shown in FIG. 2, the outer, waist elastics 170 extend continuously laterally between the first and second opposing end regions 106a, 106b and across the central region 106c of the first elastic belt 106 and between the first and second opposing end regions 108a, 108b and across the central region 108c of the second elastic belt 108. In some embodiments, some elastic strands 168 may be configured with discontinuities in areas. For example, as shown in FIG. 2, the inner, waist elastics 172 extend intermittently along the first and second elastic belts 106, 108. More particularly, the inner, waist elastics 172 extend along the first and second opposing end regions 106a, 106b and partially across the central region 106c of the first elastic belt 106. The inner, waist elastics 172 also extend along the first and second opposing end regions 108a, 108b and partially across the central region 108c of the second elastic belt 108. As such, the inner, waist elastics 172 do not extend across the entirety of the central regions 106c, 108c of the first and second elastic belts 106, 108. Thus, some elastic strands 168 may not extend continuously through regions of the first and second elastic belts 106, 108 where the first and second elastic belts 106, 108 overlap the absorbent assembly 140. In some embodiments, some elastic strands 168 may partially extend into regions of the first and second elastic belts 106, 108 where the first and second elastic belts 106, 108 overlap the absorbent assembly 140. In some embodiments, some elastic strands 168 may not extend into any region of the first and second elastic belts 106, 108 where the first and second elastic belts 106, 108 overlap the absorbent assembly 140. It is to be appreciated that the first and/or second elastic belts 106, 108 may be configured with various configurations of discontinuities in the outer, waist elastics 170 and/or the inner, waist elastic elastics 172.

In some embodiments, the elastic strands 168 may be disposed at a constant interval in the longitudinal direction. In other embodiments, the elastic strands 168 may be disposed at different intervals in the longitudinal direction. As discussed in more detail below, the belt elastic strands 168, in a stretched condition, may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt. It is to be appreciated that the chassis 102 and elastic belts 106, 108 may be configured in different ways other than as depicted in FIG. 2.

As previously mentioned, the apparatuses and methods according to the present disclosure may be utilized to transfer and/or bond discrete absorbent articles 100 and/or various components of absorbent articles 100, such as for example, chassis 102, elastic belts 106, 108, and/or leg cuffs 156. Although the following methods may be provided in the context of the diaper 100 shown in FIGS. 1 and 2, it is to be appreciated that the methods and apparatuses herein may be used with various process configurations and/or absorbent articles, such as for example, disclosed in U.S. Pat. No. 7,569,039; U.S. Patent Publication Nos. 2005/0107764 A1, 2012/0061016 A1, and 2012/0061015 A1; 2013/0255861 A1; 2013/0255862 A1; 2013/0255863 A1; 2013/0255864 A1; and 2013/0255865 A1.

Figure 4:
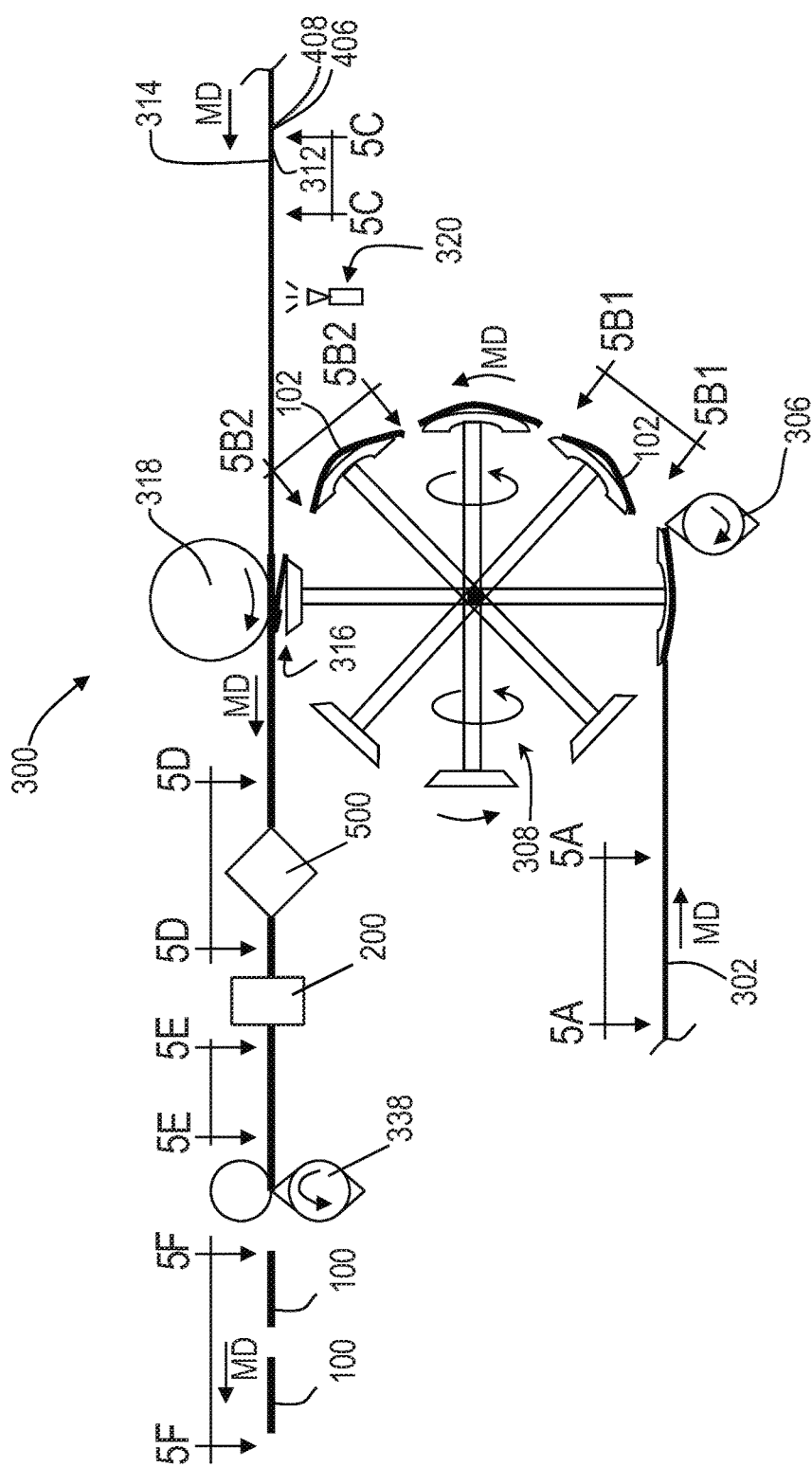
FIG. 4 is a schematic representation of a converting apparatus in accordance with one non-limiting embodiment of the present disclosure.

As previously mentioned, the apparatuses and methods according to the present disclosure may be utilized to assemble various components of absorbent articles 100. For example, FIG. 4 shows a schematic view of a converting apparatus 300 adapted to manufacture absorbent articles 100. The method of operation of the converting apparatus 300 may be described with reference to the various components of absorbent articles 100, such as described above and shown in FIGS. 1 and 2. Although the following methods are provided in the context of the absorbent article 100 shown in FIGS. 1 and 2, it is to be appreciated that various embodiments of diaper pants can be manufactured according to the methods disclosed herein, such as for example, the absorbent articles disclosed in U.S. Pat. No. 7,569,039 and U.S. Patent Publication Nos. 2005/0107764 A1; 2012/0061016 A1; and 2012/0061015 A1.

As described in more detail below, the converting apparatus 300 shown in FIG. 4 operates to advance discrete chassis 102 along a machine direction MD such that the lateral axis of each chassis 102 is parallel with the machine direction, and wherein the chassis 102 are spaced apart from each other along the machine direction. Opposing waist regions 116, 118 of the spaced apart chassis 102 are then connected with continuous lengths of advancing first and second elastic substrates 406, 408. The chassis 102 are then folded along the lateral axis to bring the first and second elastic substrates 406, 408 into a facing relationship, and the first and second elastic substrates are connected together along regions 336 intermittently spaced along the machine direction, wherein each region 336 may include one or more discrete bond sites 336a. And the elastic substrates 406, 408 are cut along the regions 336 to form a discrete belt and creating discrete absorbent articles 100, such as shown in FIG. 1.

As shown in FIGS. 4 and 5A, a continuous length of chassis assemblies 302 are advanced in a machine direction MD to a carrier apparatus 308 and cut into discrete chassis 102 with knife roll 306. The continuous length of chassis assemblies 302 may include absorbent assemblies 140 sandwiched between topsheet material 138 and backsheet material 136, leg elastics, barrier leg cuffs and the like. A portion of the chassis assembly is cut-away to show a portion of the backsheet material 136 and an absorbent assembly 140.

After the discrete absorbent chassis 102 are cut by the knife roll 306, the carrier apparatus 308 rotates and advances the discrete chassis 102 in the machine direction MD in the orientation shown in FIG. 5B1, wherein the longitudinal axis 124 of the chassis 102 is generally parallel with the machine direction MD. While the chassis 102 shown in FIG. 5B1 is shown with the second laterally extending end edge 146 as a leading edge and the first laterally extending end edge 144 as the trailing edge, it is to be appreciated that in other embodiments, the chassis 102 may be advanced in other orientations. For example, the chassis may be oriented such that the second laterally extending end edge 146 is a trailing edge and the first laterally extending end edge 144 is a leading edge. The carrier apparatus 308 also rotates while at the same time changing the orientation of the advancing chassis 102. The carrier apparatus 308 may also change the speed at which the chassis 102 advances in the machine direction MD. It is to be appreciated that various forms of carrier apparatuses may be used with the methods herein, such as for example, the carrier apparatuses disclosed in U.S. Pat. No. 7,587,966. FIG. 5B2 shows the orientation of the chassis 102 on the carrier apparatus 308 while advancing in the machine direction. More particularly, FIG. 5B2 shows the chassis 102 with the lateral axis 126 of the chassis 102 generally parallel with the machine direction MD, and wherein the second longitudinal side edge 130 is the leading edge and the first longitudinal side edge 128 is the trailing edge.

As discussed below with reference to FIGS. 3, 5C, 5D, 5E, and 5F, the chassis 102 are transferred from the carrier apparatus 308 and combined with advancing, continuous lengths of belt substrates 406, 408, which are subsequently cut to form first and second elastic belts 106, 108 on diapers 100.

With reference to FIG. 4, the chassis 102 are transferred from the carrier apparatus 308 to a nip 316 between the carrier apparatus 308 and a carrier apparatus 318 where the chassis 102 is combined with continuous lengths of advancing first elastic belt substrate 406 and second elastic belt substrate 408. The first substrate material 406 and the second substrate material 408 each define a wearer facing surface 312 and an opposing garment facing surface 314, as illustrated in FIG. 5C. The wearer facing surface 312 of the first substrate 406 may be combined with the garment facing surface 134 of the chassis 102 along the first waist region 116, and the wearer facing surface 312 of the second substrate 408 may be combined with the garment facing surface 134 of the chassis 102 along the second waist region 118. As shown in FIG. 4, adhesive 320 may be intermittently applied to the wearer facing surface 312 of the first and second substrates 406, 408 before combining with the discrete chassis 102 at the nip 316 between roll 318 and the carrier apparatus 308.

With reference to FIGS. 4 and 5D, a continuous length of absorbent articles 400 are defined by multiple discrete chassis 102 spaced from each other along the machine direction MD and connected with each other by the substrate assembly 190 which includes the second substrate 408 and the first substrate 406. As shown in FIG. 4, the continuous length of absorbent articles 400 advances from the nip 316 to a folding apparatus 500. At the folding apparatus 500, each chassis 102 is folded in the cross direction CD along a lateral axis 126 to place the first waist region 116, and specifically, the inner, body facing surface 132 into a facing, surface to surface orientation with the inner, body surface 132 of the second waist region 118. The folding of the chassis also positions the wearer facing surface 312 of the second belt substrate 408 extending between each chassis 102 in a facing relationship with the wearer facing surface 312 of the first belt substrate 406 extending between each chassis 102. As shown in FIGS. 4, 5D, and 5E, the folded discrete chassis 102 connected with the first and second substrates 406, 408 are advanced from the folding apparatus 500 to a bonder apparatus 200. The bonder apparatus 200 operates to bond, at least a portion of the region 336, which may include an overlap area 362, of the substrate assembly 190 thus creating discrete bond sites 336a. An overlap area 362 includes a portion of the second substrate 408 extending between each chassis 102 and a portion of the first substrate 406 extending between each chassis 102. As shown in FIGS. 4 and 5F, a continuous length of absorbent articles are advanced from the bonder apparatus 200 to a knife roll 338 where the regions 336 are cut into along the cross direction to create a first side seam 178 and a second side seam 180 on an absorbent article 100.

Although the absorbent article is described as having a substrate assembly that includes first and second substrates, it is to be appreciated that the absorbent article may have only one substrate or, alternatively, one or more substrates. For example, the substrate assembly may include a first substrate, a second substrate, a third substrate, and a fourth substrate. Further, it is to be appreciated that the chassis and substrate of the absorbent article may be one continuous substrate such that the overlap area is formed from the same substrate. As such, the bonder apparatus may operate to bond a continuous substrate at an overlap area to form one or more discrete bond sites.

Figure 6:
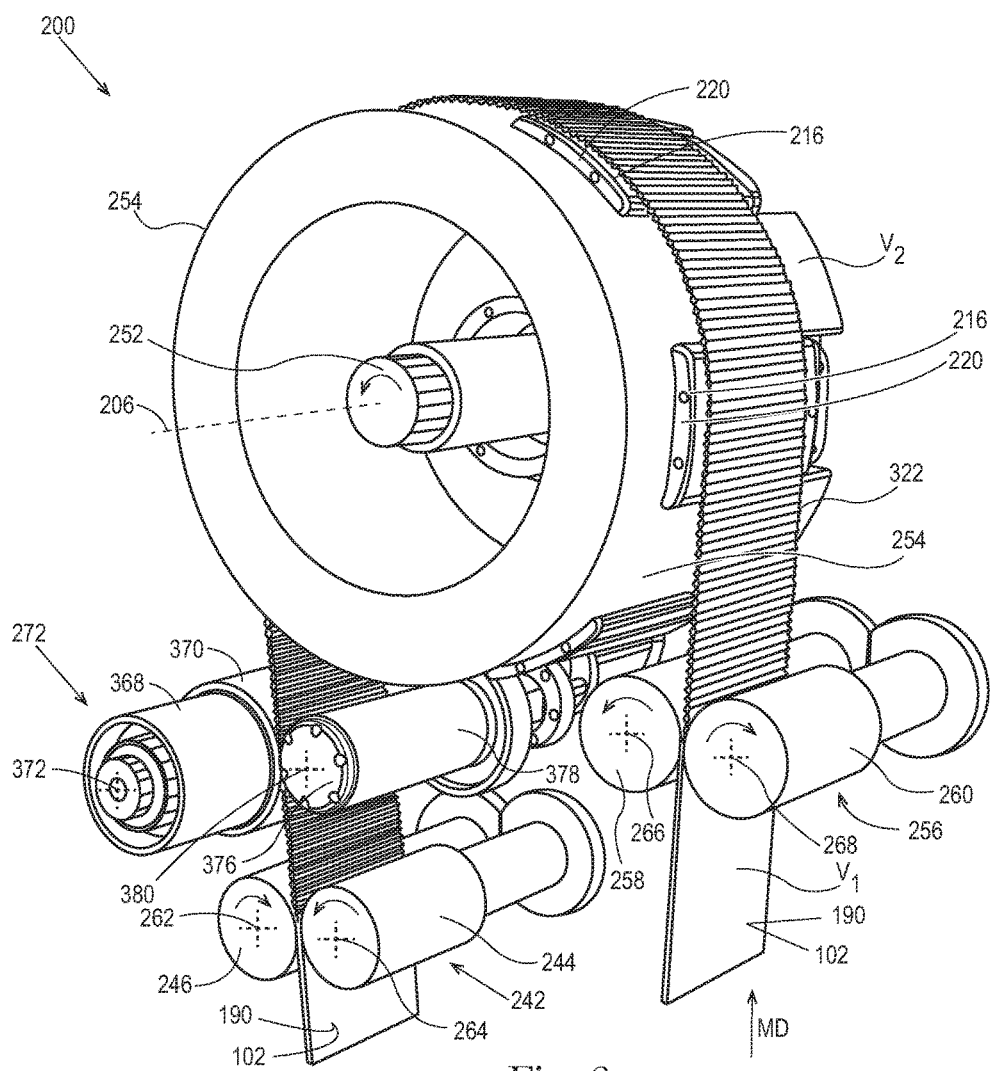
FIG. 6 is a perspective view of a bonder apparatus in accordance with one non-limiting embodiment of the present disclosure.

As previously discussed, the converting apparatus 300 may include a bonder apparatus 200. For example, FIG. 6 illustrates a perspective view of an embodiment of a bonder apparatus 200 that may be used with the methods and apparatuses herein. As shown in FIG. 6, the bonder apparatus 200 may include a shaft 252 rotatable about an axis of rotation 206. Further, the bonder apparatus 200 may include an outer circumferential surface 254 and one or more process assemblies 220. The one or more process assemblies 220 may be disposed on the outer circumferential surface 254. In some embodiments, a receiving surface 216 may be disposed on each of the process assemblies 220.

A first metering assembly 256 may be positioned adjacent the outer circumferential surface 254. The first metering assembly 256 may include a first roll 258 and a second roll 260. The first metering assembly 256 may be configured to receive a substrate assembly 190. The substrate assembly 190 advances toward the bonder apparatus at a first velocity $V_1$. The first metering assembly 256 accepts the substrate assembly at the first velocity $V_1$. More specifically, the first metering roll 258 and the second metering roll 260 are configured to rotate about a first metering axis of rotation 266 and a second metering axis of rotation 268, respectively. The first roll 258 and the second roll 260 rotate about their respective axes of rotation at a first velocity $V_1$, or the velocity at which the substrate assembly 190 is advanced toward the metering assembly 256. However, the bonder apparatus 200 may rotate about the axis of rotation 206 at a slower velocity. The bonder apparatus 200 may rotate about the axis of rotation 206 at a second velocity $V_2$. The second velocity $V_2$ may be less than the first velocity $V_1$. Consequently, the substrate assembly 190 may contract as the substrate assembly 190 exits the first metering assembly 256. This contraction may result in the substrate assembly 190 forming one or more puckers 322 as illustrated in FIG. 6.

A portion of the substrate assembly 190 may be disposed on the outer circumferential surface 254 and a portion of the substrate assembly 190 may be disposed on the process member 220 and/or the receiving surface 216. The substrate assembly 190 may be rotated about the axis of rotation 206 of the bonder apparatus 200. The substrate assembly 190 may be rotated at a second velocity $V_2$. During rotation of the substrate assembly 190 one or more process may mechanically deform one or more portions of the substrate assembly 190, which will be described in more detail herein.

Upon completion of the one or more processes, the substrate assembly 190 may be removed from the outer circumferential surface 254 of the bonder apparatus 200 and/or the receiving surface 216. In some embodiments, the substrate assembly 190 may advance to a compression assembly 272. The compression assembly 272 may include an anvil roll 368 and a bond roll 376. The anvil roll 368 may include an outer circumferential surface 370 and may be configured to rotate about an axis of rotation 372. The bond roll 376 may include an outer circumferential surface 378 and may be configured to rotate about an axis of rotation 380. The anvil roll 368 and the bond roll 376 operatively engage to bond at least a portion of the substrate assembly 190.

The substrate assembly 190 may advance through a second metering assembly 242. The second metering assembly 242 may include a third roll 244 and a fourth roll 246. The third roll 244 may rotate about a third metering axis of rotation 264 and the fourth roll 246 may rotate about a fourth metering axis of rotation 264. The third roll 244 and the fourth roll 246 rotate at the second velocity $V_2$. The substrate assembly 190 advances toward the second metering assembly 242 at a second velocity $V_2$. The substrate assembly 190 passes through the second metering assembly 242, and advances away from the second metering assembly 242 at a second velocity $V_2$. The second metering assembly 242 may ensure that the substrate assembly 190 continues to advance at the second velocity $V_2$ as the substrate assembly 190 passes through the compression assembly 272.

Figure 6A:
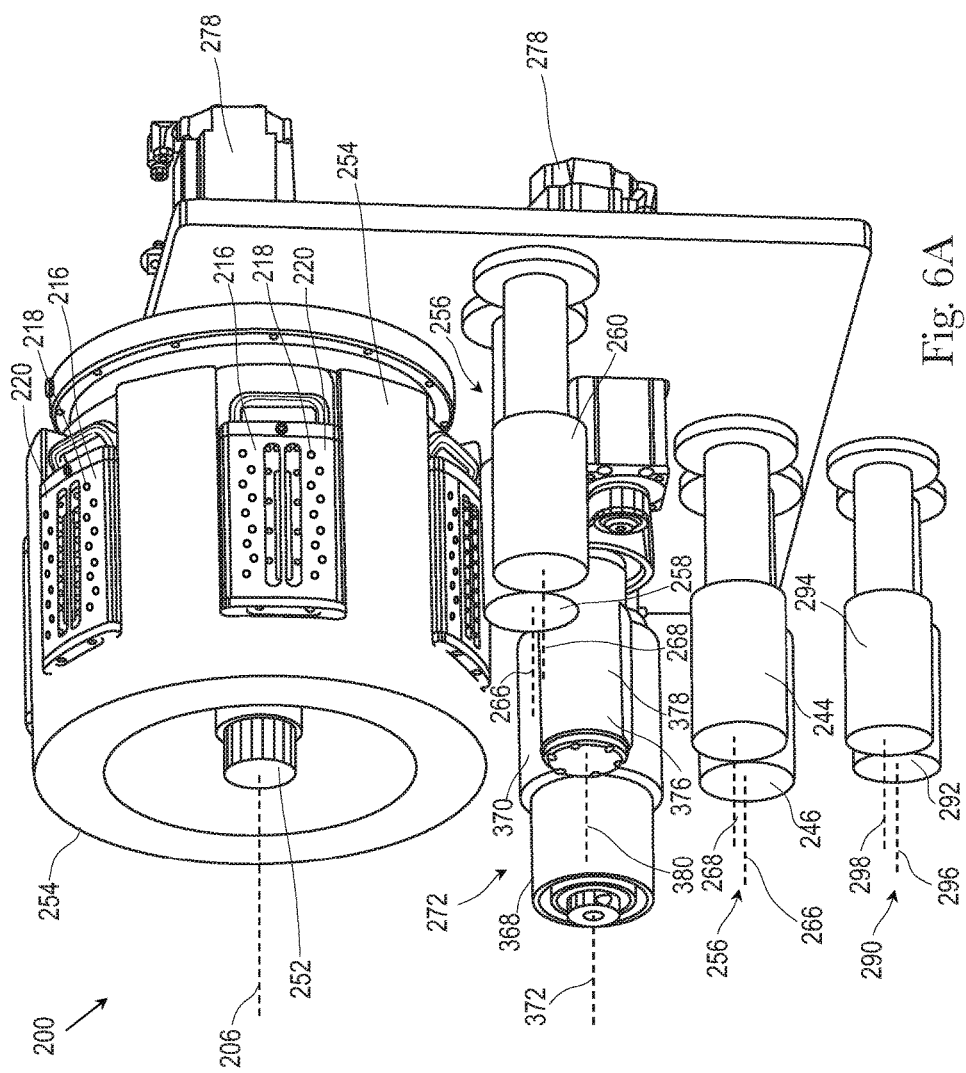
FIG. 6A is a perspective view of a bonder apparatus in accordance with one non-limiting embodiment of the present disclosure.

Downstream of the second metering assembly 242 may be a third metering assembly 290, as illustrated in FIG. 6A. The substrate assembly 190 may advance at the second velocity $V_2$ between the second metering assembly 242 and the third metering assembly 290. The third metering assembly 290 may include a fifth roll 292 and a sixth roll 294 that are each configured to rotate about a fifth metering axis of rotation 296 and a sixth metering axis of rotation 298, respectively. The third metering assembly 290 may be configured to return the substrate assembly 190 to the first velocity $V_1$. Thus, the fifth roll 292 and the sixth roll 298 may each rotate about their respective axes of rotation 296, 298 at the first velocity $V_1$. As the substrate assembly 190 passes through the fifth roll 292 and the sixth roll 294, the substrate assembly 190 may accelerate to the first velocity $V_1$. The substrate assembly 190 may advance away from the third metering assembly 290 as the first velocity $V_1$. Further, the third metering assembly 290 may expand the substrate assembly 190.

It is to be appreciated that the metering assembly may be any configuration of rolls and/or conveyors that allows the tension on the substrate assembly to be isolated on either side of the metering assembly. Examples of metering assemblies may include a vacuum conveyor, one or more rollers positioned to s-wrap the substrate assembly, one or more driven rolls, and/or a vacuum roll.

As illustrated in FIG. 6A, one or more process assemblies 220 may be disposed on the outer circumferential surface 254 of the bonder apparatus 200. Further a receiving surface 216 may be disposed on each process assembly 220. It is to be appreciated that the receiving surface 216 may be part of the process assembly 220 or separate from the process assembly 220. The receiving surface may include one or more apertures 218. The one or more apertures 218 may correspond to the operations of the process assembly 220. Further, the apertures 218 may be used to control the position of the substrate assembly. The one or more apertures 218 may also be referred herein as fluid apertures and vacuum apertures. For example, the one or more apertures 218 may be used to transfer fluid, such as air, through the one or more vacuum apertures in a direction toward the axis of rotation 206 causing the substrate assembly to be held against the receiving surface 216, which forms a vacuum force. The one or more apertures 218 may also be used to transfer fluid, such as air, through the one or more fluid apertures in a direction away from the axis of rotation 206 causing the substrate assembly to be forced away from the receiving surface 216, which forms a pressure force. In some embodiments, certain apertures 218 may be configured to supply a vacuum force on the substrate assembly and other apertures 218 may be configured to supply a pressure force on the substrate assembly. However, it to be appreciated that the same aperture 218 may be used to supply both a vacuum force and a pressure force on at least a portion of the substrate assembly.

The bonder apparatus 200 may be driven by one or more drive members 278. Further each of the metering assemblies and the compression assembly may be driven by one or more drive members 278. Each drive member may be a motor. The motor may be any device that transmits rotational energy to the member. The motor may be operatively linked or operatively engaged with the assemblies using any technique known to those skilled in the art such as, for example, a gear to gear connection, transmission belting and pulleys, gearboxes, direct couplings, and the like or any combination thereof.

Figure 7:
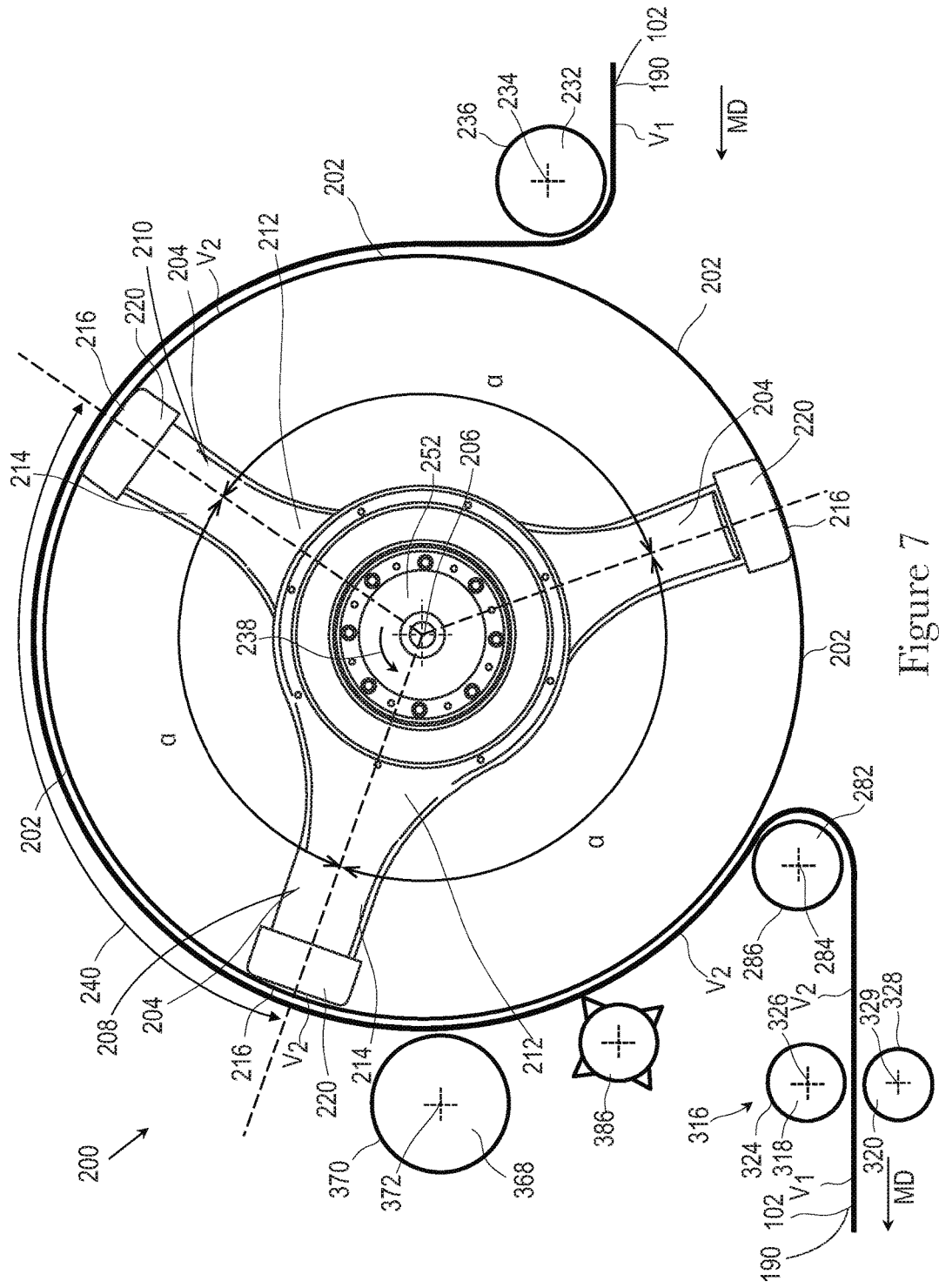
FIG. 7 is a side view of a bonder apparatus in accordance with one non-limiting embodiment of the present disclosure.

In some embodiments, the bonder apparatus 200 may be configured as illustrated in FIG. 7. The bonder apparatus 200 may include a shaft 252 rotatable about an axis of rotation 206. Further, the bonder apparatus 200 may include a support surface 202 and two or more members 204. The two or more members 204 and the support surface 202 may be adapted to rotate about an axis of rotation 206. The support surface 202 may extend between adjacent members 204. In some embodiments, the bonder apparatus 200 may include a first member 208 and a second member 210, adjacent the first member 208. Each of the first member 208 and the second member 210 may be adapted to rotate about the axis of rotation 206. However, each of the first member and the second member do not rotate relative to one another. Each of the first member 208 and the second member 210 may include a proximal end portion 212 adjacent to the axis of rotation 206 and a distal end portion 214 opposite the proximal end portion 212. The proximal end portion of each of the first member and the second member may be connected to the shaft member 252. The shaft 252 may be driven by a drive member, such as a motor. The motor may be any device that transmits rotational energy to the member. The motor may be operatively linked or operatively engaged with the member using any technique known to those skilled in the art such as, for example, a gear to gear connection, transmission belting and pulleys, gearboxes, direct couplings, and the like or any combination thereof.

The bonder apparatus 200 may also include a receiving surface 216. The receiving surface 216 may be positioned at the distal end portion 214 of each member. The receiving surface 216 may be configured to receive a portion of the substrate assembly, which will be discussed in more detail herein. The receiving surface 216 may include one or more apertures 218, also referred herein as fluid apertures and vacuum apertures, as previously described.

In some embodiments, the bonder apparatus 200 may also include a process assembly 220. The process assembly 220 may be positioned adjacent the receiving surface 216. The process assembly 220 may be used, for example, to bond the substrate assembly and/or cut the substrate assembly, and/or to alter in some other manner the substrate assembly. It is to be appreciated that the receiving surface 216 may be part of the process assembly 220, or the receiving surface 216 may be a separate component from the process assembly 220.

Still referring to FIG. 7, the support surface 202 may be attached to a portion of at least one of a member 204, a process assembly 220, and a receiving surface 216. More specifically, for example, the support surface 202 may be attached to the receiving surface 216 of the first member 208 and may extend to and be attached to the receiving surface 216 of the adjacent, second member 210. The support surface 202 substantially surrounds to the axis of rotation 206. Further the support surface 202 may be positioned at a substantially constant radius about the axis of rotation 206.

Figure 7A:
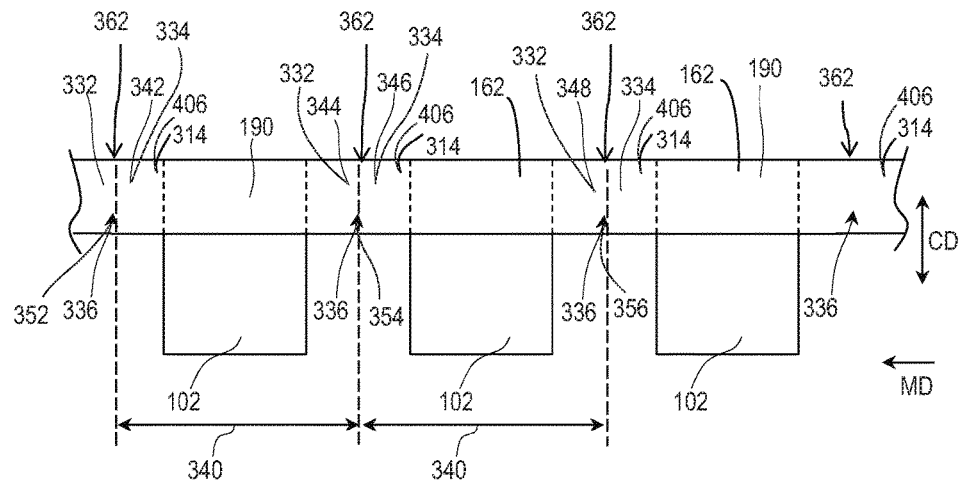
FIG. 7A is a top view of multiple discrete chassis attached to a first elastic belt substrate and a second elastic belt substrate in accordance with one non-limiting embodiment of the present disclosure.
Figure 7B:
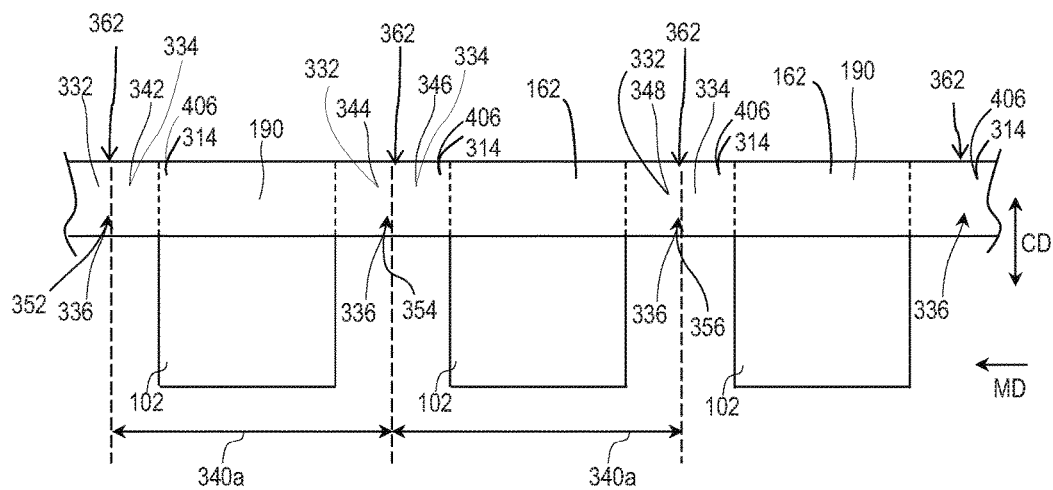
FIG. 7B is a top view of multiple discrete chassis attached to a first elastic belt substrate and a second elastic belt substrate in accordance with one non-limiting embodiment of the present disclosure.

Referring to FIGS. 7, 7A, and 7B, the substrate assembly 190 with the folded chassis 102 may advance in the machine direction MD to the bonder apparatus 200. As previously discussed, a substrate assembly 190 may include a first substrate and a second substrate in a facing relationship. It is to be appreciated that a substrate assembly 190 may include any number of substrates in any partially overlapping configuration. The first substrate and the second substrate may be used to form a first elastic belt and a second elastic belt of the absorbent article. Thus, the first substrate and the second substrate may be elastically extensible in at least one of the machine direction MD and the cross direction CD. The first and second substrates may include regions 336 intermittently spaced along the machine direction, wherein each region 336 may include a leading portion 332 and a trailing portion 334. For example, as illustrated in FIG. 7A, a first region 352 may include a first leading portion 334 and a subsequent or adjacent region in the machine direction MD, such as a second region 354, may include a first trailing portion 344 and a second leading portion 346 and yet another subsequent or adjacent region in the machine direction MD, such as a third region 356, may include a second trailing portion 348.

Each leading portion and trailing portion may define a process product pitch 340, 340a. More specifically, for example, a process product pitch 340, 340a refers to the distance in the machine direction MD between the area at which a leading edge portion and a trailing edge portion meet in a first region to the area at which a leading edge portion and a second trailing edge portion in a subsequent, adjacent region meet, as illustrated in FIGS. 7A and 7B. The process product pitch may change based on the size of the absorbent article, the amount of elasticity of the substrate assembly, and the process tension placed on the substrate assembly as the substrate assembly is advanced in the machine direction MD. It is to be appreciated that the process product pitch includes the process tension placed on the substrate during processing.

As illustrated in FIG. 7, the substrate assembly 190 may advance in the machine direction MD toward the bonder apparatus 200 at a first velocity $V_1$. Further, the substrate assembly 190 may be held at a process tension as the substrate assembly is advanced toward the bonder apparatus 200. An entry metering roll 232 configured to rotate about an axis of rotation 234 and including an outer circumferential surface 236 may be used to transfer the substrate assembly 190 onto the bonding apparatus 200. The substrate assembly 190 may be disposed on a portion of the outer circumferential surface 236 of the entry metering roll 232 as the substrate assembly is transferred to the bonder apparatus 200. Further, the entry metering roll 232 and the bonder apparatus 200 may be configured to relax or contract the substrate assembly 190. More specifically, the substrate assembly 190 advances toward the entry metering roll 232 at a first velocity $V_1$. The entry metering roll 232 continues to advance the substrate assembly 190 at the first velocity $V_1$. However, the bonder apparatus 200 may rotate about the axis of rotation 206 at a second velocity $V_2$, which is less than the first velocity $V_1$. This results in contracting or relaxing the substrate assembly 190, which may result in one or more puckers 322 forming in the substrate assembly 190, as illustrated in FIG. 6. It is to be appreciated that for minor changes in velocity the substrate assembly may not form one or more puckers 322.

As previously discussed, the receiving surface 216 may receive a region 336 of the substrate assembly 190. More specifically, the first leading portion 342 may be disposed on the receiving surface 216 of the first member 204 as the first member 204 rotates at the second velocity about the axis of rotation 206. The vacuum apertures may be used to secure the region of the substrate assembly to the receiving surface 216. It is also to be appreciated that a mechanical device, such as a clamp or a position control apparatus, may be used to exert a mechanical force on the substrate assembly, which secures the substrate assembly to the bonder apparatus 200.

A second member 210 may also rotate about the axis of rotation 206 in the direction indicated by arrow 238. The second member 210 may rotate at the second velocity and may receive the subsequent region 336 of the substrate assembly 190. Similar to above, the first trailing portion 344 and the second leading portion 346 of the substrate assembly 190 may be disposed on the receiving surface 216 of the second member 210 as the second member 210 rotates at the second velocity. The vacuum apertures and/or a mechanical device may be used to secure the substrate assembly to the bonder apparatus 200.

Once the region 336 of the substrate assembly 190 is disposed on the receiving surface 216 of the first member 208, the first member 208 continues to rotate at a constant velocity such that the first member 208 rotates the substrate assembly 190 at a second velocity $V_2$. The second velocity $V_2$ may be less than or equal to the first velocity $V_1$. Similarly, once the region 336 of the substrate assembly 190 is disposed on the receiving surface 216 of the second member 210, the second member 210 continues to rotate at a constant velocity such that the second member 208 rotates the substrate assembly 190 at the second velocity $V_2$.

The first member 208 and the second member 210 may be separated by a process angle α. The process angle between each adjacent member remains constant as the members rotate about the axis of rotation.

In some embodiments, the second velocity $V_2$ is less than $V_1$. When the second velocity is less than the first velocity, the tension of the substrate assembly disposed on the first member 208, the second member 210, and the support surface 202 between the first member 208 and the second member 210 may decrease. More specifically, the substrate assembly 190 may be relaxed, also referred to herein as being contracted, such that the process tension is decreased to a relaxed tension. The substrate assembly includes one or more elastic strands or an elastic substrate, such as an elastic film. The substrate assembly may be relaxed, or contracted, when the tension placed on the elastic stands and/or elastic substrate is reduced or removed. In some embodiments, the substrate assembly may be contracted to a degree that one or more puckers form in the substrate assembly. A pucker may form when the substrate assembly is allowed to relax to a degree such that a portion of the substrate assembly deflects out of plane.

Stated another way, each region 336 may be disposed on the receiving surface 216 and/or the process assembly 220, and the central portion 330 of the substrate assembly 190, which is the portion of the substrate assembly between each of the adjacent regions 336, as illustrated in FIGS. 7A and 7B, may be disposed on the support surface 202. The product arc length 240 is the distance measured along the support surface, or along the circumferential path of the support surface, between a leading portion and a subsequent, adjacent trailing portion, such as the first leading portion and the first trailing portion. The product arc length 240 may be substantially equal to or less than the process product pitch 340, 340a. More specifically, as the substrate assembly 190 is transferred onto each member and support surface and rotates about the axis of rotation 206, the substrate assembly 190 may maintain the same process tension while disposed on the bonder apparatus 200 as the process tension of the substrate assembly 190 while being advanced toward the bonder apparatus 200, or the tension of the substrate assembly may be decreased to a relaxed tension, which is less than the process tension. In summary, as the substrate assembly 190 rotates about the axis of rotation 206, the product arc length 240 may be substantially the same as the process product pitch, or the product arc length 240 may be less than the process product pitch 340, 340a.

It is to be appreciated that to maintain the process tension of the region 336, various position control devices may be used. In some embodiments, as previously discussed, the one or more apertures 218 disposed on the receiving surface 216 may be configured to secure the substrate assembly 190 to the receiving surface 216 with a vacuum force. In some embodiments, a mechanical device may be used to apply a mechanical force to secure the substrate assembly 190 to the receiving surface 216. For example, the bonder apparatus 200 may include a clamping device. The clamping device 320 may be configured to engage a portion of the region 336 or some other portion of the substrate assembly. Further, a position control apparatus 450, such as that illustrated in FIG. 7C, oriented adjacent to the bonder apparatus may be used to secure the substrate assembly 190 to the bonder apparatus 200.

Figure 8:
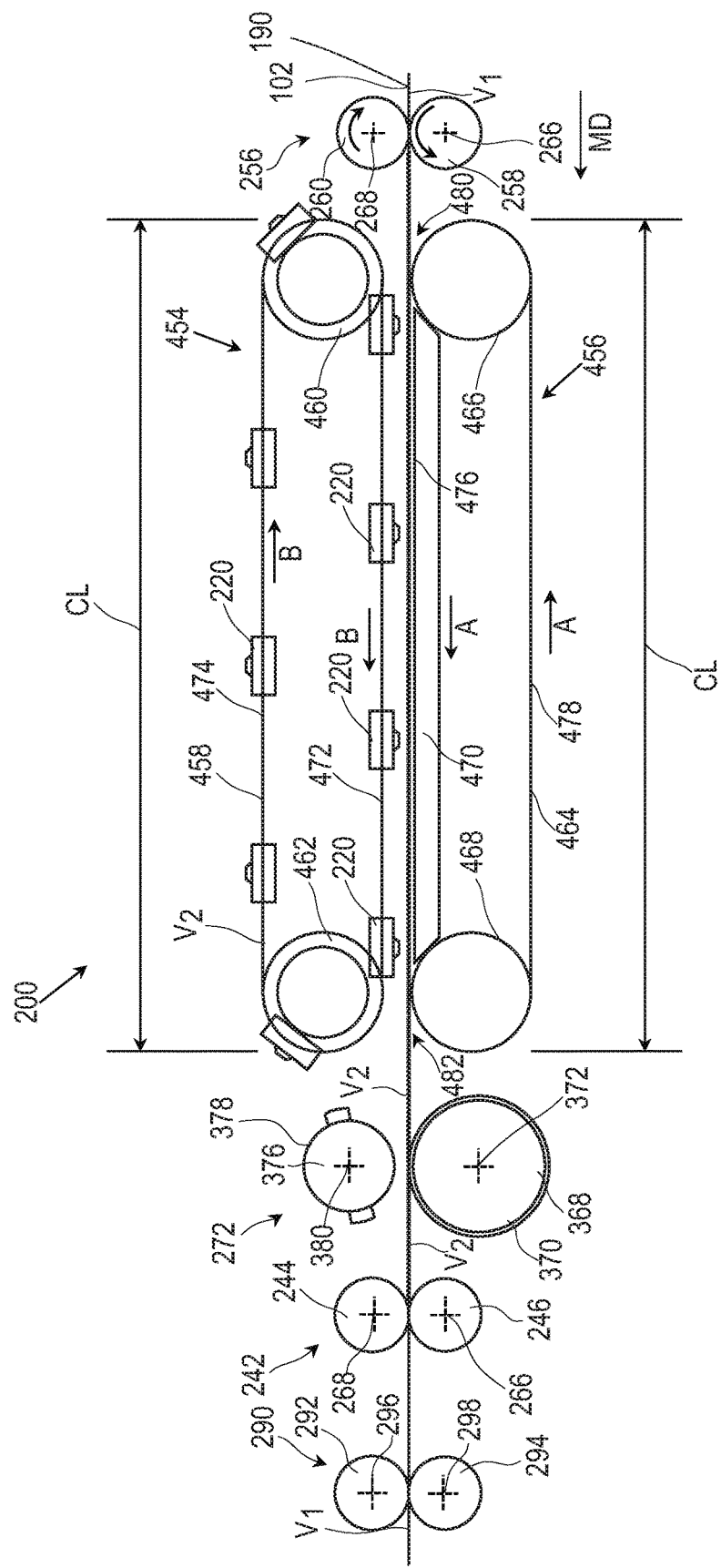
FIG. 8 is a side view of a bonder apparatus in accordance with one non-limiting embodiment of the present disclosure.

Similar to the above, it is to be appreciated that, in some embodiments, a third member may rotate about the axis of rotation 206 to receive the second trailing portion 348. As illustrated in FIGS. 7 and 8, each member may be separated by a process angle α. Each member may be positioned an equal distance from each adjacent member. For example, if the bonder apparatus 200 included two members, each member would be separated by about 180 degrees. Similarly, if the bonder apparatus 200 included three members, each member would be separated by about 120 degrees. The bonder apparatus 200 may include any number of members 204.

The regions 336 disposed on each of the receiving surfaces may undergo one or more process, such as bonding, cutting, or scoring, while rotating about the axis of rotation 206 at the second velocity $V_2$. After one or more processes are complete, each member 204 may rotate to a position adjacent to an exit guide roll 282 or, stated another way, to a position at which the substrate assembly 190 may be removed from the member. The exit guide roll 282 may be configured to rotate about an axis of rotation 284 and includes an outer circumferential surface 286. The substrate assembly 190 may be transferred from the receiving surface 216 and/or the support surface 202 to the outer circumferential surface 286 of the exit guide roll 282, as illustrated in FIGS. 7 and 8. Pressure may be used to aid in the transfer of the substrate assembly 190. The exit guide roll 282 may rotate about the axis of rotation 284 at a second velocity $V_1$.

In some embodiments, the substrate assembly 190 may advance from the exit guide roll 282 to an exit metering assembly 316, as illustrated in FIG. 7. The exit metering assembly 316 may include a first exit roll 318 and a second exit roll 320. The first exit roll 318 may include a first outer circumferential surface 324 and may be configured to rotate about an axis of rotation 326. The second exit roll 320 may include a second outer circumferential surface 328 and may be configured to rotate about an axis of rotation 329. The first exit roll 318 and the second exit roll 320 may each rotate at a first velocity $V_1$. The first exit roll 318 and the second exit roll 320 engage the substrate assembly 190 such that the substrate assembly 190 accelerates to the first velocity $V_1$. The substrate assembly 190 advances away from the exit metering roll 282 at the first velocity $V_1$. Further, the exit metering assembly may expand the substrate assembly such that the leading portion and the trailing portion return to the process product pitch. The members continue to rotate about the axis of rotation 206 at the second velocity after the substrate assembly 190 has been removed.

Absorbent articles come in a variety of sizes. For example, one absorbent article may include a larger chassis and a larger belt as compared to another absorbent article which may include a smaller chassis and a smaller belt, as illustrated in FIGS. 7B and 7A, respectively. Thus, the previously described bonder apparatus 200 may be used such that the absorbent article including the larger chassis and the larger belt can be manufactured on substantially the same equipment as the absorbent article including the smaller chassis and the smaller belt. This prevents manufacturers from having to switch out equipment or to make large modifications to the equipment for manufacturing different sized articles, which is costly and time consuming. The bonder apparatus in combination with the metering rolls may be used to reduce the process product pitch of the absorbent article such that once the substrate assembly exits the first metering roll or the entry metering roll, the product arc length becomes the same even though the final absorbent articles are of two different sizes.

For example, the same bonder apparatus 200 may be used to process the substrate assembly illustrated in 7A and the substrate assembly illustrated in FIG. 7B. As shown, the substrate assembly of FIG. 7A has a shorter process product pitch 340 than the process product pitch 340a of the substrate assembly of FIG. 7B. However, the metering assembly or entry metering roll allows the substrate assembly to contract such that the product arc length of the substrate assembly illustrated in FIG. 7A would be substantially the same as the product arc length of the substrate assembly illustrated in FIG. 7B. The second metering assembly or the exit metering assembly returns the substrate assembly to the process product pitch. Thus, substrate assemblies having various sizes may be processed and transferred on the same bonder apparatus.

The bonder apparatus 200 may be designed for a minimum product pitch based on the diameter of the bonder apparatus 200 and/or the number of members 204. Thus, for each process product pitch that is greater than the minimum process product pitch of the bonder apparatus 200, the product arc length of the substrate assembly will be less than the product pitch of the substrate assembly. It is to be appreciated that the second velocity at which the substrate assembly of FIG. 7A is processed may be different than the second velocity at which the substrate assembly of FIG. 7B is processed. It is also to be appreciated at the first velocity may be greater than or equal to the second velocity.

As previously discussed, the bonder apparatus 200 may include a process assembly 220. The process assembly 220 may be used to bond, cut, score, or perform some other mechanical deformation on the substrate assembly 190. In some embodiments, the process assembly 220 may be required to interact with additional apparatuses. For example, as illustrated in FIG. 7, the process assembly 220 may operatively engage an anvil roll 368 positioned adjacent the receiving surface 216 and/or the support surface 202. The anvil roll 368 includes an anvil roll outer circumferential surface 370 and may be adapted to rotate about an anvil roll axis of rotation 372. The outer circumferential surface 270 may operatively engage a portion of the process assembly 220 forming a bond, for example, in the substrate assembly 190. In some embodiments, for example, the process assembly 220 may operatively engage a cutting device 386 positioned adjacent the bonder apparatus 200, as illustrated in FIG. 7. The cutting device 386 may include one or more blades configured to operatively engage a portion of the process assembly 220 forming a cut and/or score line in the substrate assembly 190.

Figure 7C:
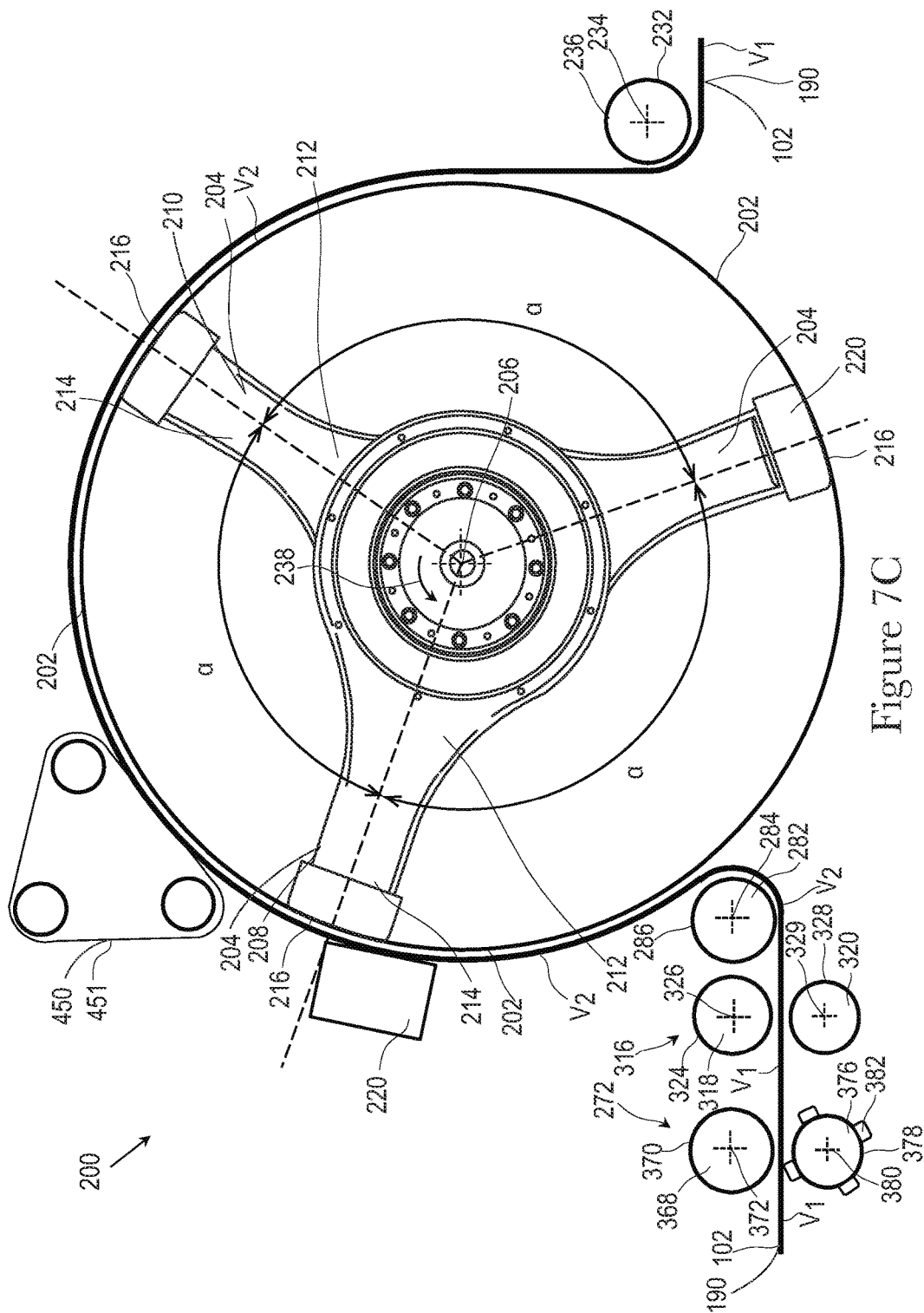
FIG. 7C is a side view of a bonder apparatus in accordance with one non-limiting embodiment of the present disclosure.

In some embodiments, as illustrated in FIG. 7C, a compression assembly 272 may be positioned downstream of the bonder apparatus 200. The compression assembly 272 may include an anvil roll 368 and a bond roll 376. Similar to the above, the anvil roll 368 may include an anvil roll outer circumferential surface 370 that may be used to operatively engage the bond roll 376. The bond roll 376 may be configured to rotate about an axis of rotation 380 and may include an outer circumferential surface 378. Further, one or more press members 382 may extend radially outward from the outer circumferential surface 378 of the bond roll 376. The substrate assembly 190 may be removed from the bonder apparatus 200, advance through a metering assembly such that the substrate assembly continues to advance at a constant velocity or accelerates to the first velocity $V_1$, and subsequently advances to the compression assembly 272 at the first velocity $V_1$. The bond roll 376 and the anvil roll 368 engaged the substrate assembly. More specifically, the press member 382 of the bond roll 376 may engage the outer circumferential surface 370 of the anvil roll 368 bonding a portion of the substrate assembly 190. It is to be appreciated that the substrate assembly 190 may be advanced to any downstream process.

The process assembly 220 may be part of the bonder apparatus 200 as illustrated in FIGS. 6, 6A, and 7. The process assembly 220 may also be positioned adjacent to the bonder apparatus 200 as illustrated in FIG. 7C. It is also to be appreciated the bonder apparatus 200 may include one or more processes assemblies 220 and one or more process assemblies 220 may be positioned adjacent to the bonder apparatus 200.

In some embodiments, the bonder apparatus 200 may be configured as illustrated in FIG. 8. The substrate assembly 190 may advance towards the bonder apparatus 200 at the first velocity $V_1$. The substrate assembly 190 may enter the first metering assembly 256. Similar to the above, the first metering assembly 256 may include a first roll 258 and a second roll 260. Each of the first roll 258 and the second roll 260 may be configured to rotate about a first metering axis of rotation 266 and a second metering axis of rotation 268, respectively. The first roll 258 and the second roll 260 may be configured to rotate at the first velocity $V_1$. The substrate assembly 190 may engage the first roll 258 and the second roll 260.

The bonder apparatus 200 may be positioned downstream of the first metering assembly 256. The bonder apparatus may include a first transition apparatus 454 and a second transition apparatus 456. The first transition apparatus 454 and the second transition apparatus 456 define an entry region 480 and an exit region 482, opposite the entry region 480. The first transition apparatus 454 may include a first conveyor 458. The first conveyor 458 may include a conveyor length CL extending in the machine direction MD and a conveyor width (not shown) extending in a direction substantially perpendicular to the machine direction MD. The conveyor length CL may be long enough such that one or more processes may be performed on the substrate assembly 190. The conveyor width may be wide enough such that at least a portion of the substrate assembly 190 contacts the first conveyor 458. The first conveyor 458 may also include a first internal surface 472 and a first external surface 474, opposite the first internal surface 472. The first external surface 474 may be in facing relationship with the substrate assembly 190. The first internal surface 472 of the first conveyor 458 may extend around a portion of a first leading roller 460 and a first trailing roller 462. Each of the first leading roller 460 and the first trailing roller 462 may be may be driven by one or more drive members, as previously discussed. The first conveyor 458 may traverse in a direction indicated by arrow B.

The bonder apparatus 200 may include one or more process assemblies 220. The process assemblies 200 may be disposed on the first conveyor 458. The process assembly 220 may be configured to mechanically deform the substrate assembly 190. Each of the process assembly 220 may be configured to rotate with the first conveyor 458. The first conveyor 458 may rotate at a second velocity $V_2$, which is less than or equal to the first velocity $V_1$.

The bonder apparatus 200 may also include a second transition apparatus 456 positioned adjacent to the first transition apparatus 454. The second transition apparatus 456 may include a second conveyor 464. The second conveyor 464 may include a conveyor length CL extending in the machine direction MD and a conveyor width (not shown) extending in a direction substantially perpendicular to the machine direction MD. The conveyor length CL may be long enough such that the substrate assembly 190 is supported while one or more processes are being performed on the substrate assembly. Stated another way, the conveyor length CL of the first conveyor 458 may be substantially the same length as the conveyor length CL of the second conveyor 464. The conveyor width may be wide enough such that at least a portion of the substrate assembly 190 contacts the second conveyor 464. The second conveyor 464 may also include a second internal surface 476 and a second external surface 478, opposite the second internal surface 476. The second external surface 478 may be in facing relationship with the substrate assembly and may be configured to engage at least a portion of the substrate assembly 190. The second internal surface 476 of the second conveyor 464 may extend around a portion of a second leading roller 466 and a second trailing roller 468. Each of the second leading roller 466 and the second trailing roller 468 may be may be driven by one or more drive members, as previously discussed. The second conveyor 464 may traverse in a direction indicated by arrow A.

The bonder apparatus 200 may include a support surface 470 positioned adjacent the second internal surface 476 of the second conveyor 464. In some embodiments, the one or more process assemblies 220 may engage the support surface 470 to mechanically deform the substrate assembly 190. In some embodiments, the support surface 470 may also include one or more vacuum apertures (not shown). The vacuum apertures may be used to transfer fluid, such as air, so that the substrate assembly 190 may be held against the second external surface 478 of the second conveyor 464.

The first conveyor 458 and the second conveyor 464 may transverse at a second velocity $V_2$. As previously discussed, the second velocity may be less than or equal to the first velocity, which is the velocity at which the substrate assembly is advanced toward the bonder apparatus 200. In embodiments where the second velocity is less than the first velocity, the substrate assembly 190 may gather, which may or may not result in the formation one or more puckers, between the first metering assembly 256 and the entry region 480 of the bonder apparatus 200. Stated another way, the substrate assembly 190 may contract between the first metering assembly 256 and the entry region 480 of the bonder apparatus 200 such that the process product pitch, or the distance between a leading portion and an adjacent trailing portion, is reduced. The substrate assembly 190 may be advanced by each of the first transition apparatus 454 and the second transition apparatus 456 in the machine direction MD in this contracted state. One or more process assemblies may perform one or more processes on the substrate assembly 190 as the substrate assembly 190 is being advanced in the machine direction MD.

Once the one or more processes are complete, the substrate assembly 190 may be advanced to the exit region 482 of the bonder apparatus 200. The substrate assembly 190 may advance through the exit region 482 at the second velocity $V_2$. As previously discussed, the substrate assembly 190 may advance to a compression assembly 272, which may bond at least a portion of the substrate assembly 190. Downstream of the compression assembly 272 may be a second metering assembly 242. The second metering assembly 242 may control the advancement of the substrate assembly 190 such that the substrate assembly 190 continues to advance at the second velocity $V_2$ from the exit region 482 of the bonder apparatus 200 through the compression assembly 272 and upon advancing through the second metering assembly 242. Thus, the second metering assembly 242 may include a third roll 244 and a fourth roll 246 configured to rotate about their respective axes of rotation at the second velocity V$_2$.

In some embodiments, a third metering assembly 290 may be positioned downstream of the second metering assembly 242. The third metering assembly 290 may be configured to return the substrate assembly to the first velocity V$_1$, or the velocity at which the substrate assembly should be advanced to subsequent processes. Thus, the third metering assembly 290 may include a fifth roll 292 and a sixth roll 294 configured to rotate about their respective axes of rotation at the first velocity V$_1$. The substrate assembly 190 may then exit the third metering assembly 290 at the first velocity V$_1$. Once the substrate assembly 190 is returned to the first velocity V$_1$, the distance between the leading portion and the subsequent trailing portion should be returned to the process product pitch.

It is to be appreciated that the second transition apparatus 456 may also include one or more process assemblies 220. Further, in some embodiments, the first transition apparatus 454 may not include one or more process assemblies 220 and may include a support surface 470.

As previously discussed, the process assembly 220 may be used to mechanically deform the substrate assembly. The mechanical deformation may be in the form of, for example, bonding, cutting, and/or scoring. In some embodiments, to bond the substrate assembly, the process assembly may include a seaming device that bonds using hot air or an ultrasonic device.

For example, in some embodiments, the process assembly 220 may include a seaming station 548, such as disclosed in U.S. Pat. No. 8,778,127 and U.S. Patent Publication Nos. 2014/0110053 and 2014/0305593. The region 336 of the first and second belt substrates 406, 408, or the substrate assembly 190 may be positioned on the receiving surface 216 coincident with the seaming station 548. The seaming station 548 may be located radially inward from the receiving surface 216 and may be configured to bond a portion of the region 336 as the substrate assembly 190 is transferred by the bonder apparatus 200. Each seaming station 548 may include a fluid nozzle 578 and a press member 580, as illustrated in FIG. 9. As the member 204 rotates, fluid nozzles 578 of the seaming station 548 move radially outward toward the receiving surface 216. In addition, a fluid is heated to a temperature sufficient to at least partially melt at least a portion of the region 336 of the substrate assembly 190. The fluid nozzles direct a jet of the heated fluid onto at least a portion of the region 336 of the substrate assembly 190, which may include a first elastic substrate 406 and a second elastic substrate 408. The heated fluid partially melts at least a portion of the region 336. As the member 204 continues to rotate about the axis of rotation 206, the fluid nozzles retract radially inward from the receiving surface 216 and a press member 580 shifts radially outward toward the receiving surface 216. The press member then compresses the partially melted overlap area against the outer circumferential surface 370 of the anvil roll 368, creating one or more discrete bond sites 336a, as shown in FIG. 5E, between the first and second substrates. As the member 204 continues to rotate, the press member retracts radially inward from the receiving surface 216.

The press member 580 may be substantially rectangular in shape and defined by a press member top face, a press member bottom face, and a press member length. The press member 580 may include substantially square-shaped projections extending outwardly from the press member top face. The projections may be arranged into two or more rows. However, it is to be appreciated that the projections 423 may be regularly or irregularly spaced in various configurations and may be oriented in various directions. The projections 423 may have a circular, oval, or various other shapes. The projections 423 may have a height in the range of about 0.5 millimeters to about 5 millimeters. In some embodiments, the projections may have a width in the range of about 2 millimeters to about 10 millimeters, or between about 4 millimeters to about 6 millimeters.

It is also to be appreciated that the press member 386 may be discontinuous along the width of the press member 386 such that multiple segments of the press member 386 may define the press member length 387. In some embodiments, multiple segments of the press member may act independently to compress the region with different amounts of pressure. For example, each segment of the press member 386 may have an individual spring member, with each spring member designed to apply a different amount of force to different parts of the region. By applying different amounts of force in different locations, it may be possible to bond through different numbers of substrate layers or materials along the region. By selectively compressing portions with more or less force, portions of the substrates with fewer layers or different materials will not be over compressed and portions of the substrates with more layers or different materials will not be under compressed. In some embodiments, the press member may have more than one segment with each segment having different shaped projections, or may have different configurations of projections along the press member length.

Each heating apparatus 384 provides a pressurized fluid source for delivery of heated, pressurized fluid, such as air for example, to the fluid nozzle 578. In some embodiments, a valve may control egress of the fluid from the heating apparatus 384 and into a fluid nozzle 578. Each heating apparatus 384 is operatively connected to the press member 580.

The seaming station 548 may also include a fluid nozzle 578. The fluid nozzle 578 may include one or more fluid orifices where the heated, pressurized fluid is released from the fluid nozzle 578. Each heating apparatus 384 may be immovably connected with a separate fluid nozzle 578. The fluid orifices 420 may be circular and may extend in a row along the fluid nozzle 578. Although, it is to be appreciated that the fluid orifices 420 may be arranged in various configurations. Also, it is to be appreciated that the fluid orifice may have an oval, square, or various other shapes. The fluid orifice 360 may have a diameter ranging from about 0.1 millimeters to about 6 millimeters.

The seaming station 548 may be positioned in a first configuration. In the first configuration, the fluid nozzles 578 are positioned radially outward near the receiving surface 216, while the press member 580 is positioned radially inward, away from the receiving surface 216. In addition, the fluid nozzles 578 are positioned at the same circumferential location as the projections 423 of the press member 386, such that the heated fluid is directed to the same locations on the region that will subsequently be compressed by the press member 580.

As the member 204 continues to rotate, the substrate assembly 204 and chassis 102 continues to be disposed on the receiving surface 216 and/or the support surface. At the same time, a jet of heated, pressurized fluid is directed from the heating apparatuses 384 out of the fluid nozzles 578 and onto the at least a portion of the region 336 of the first and second substrates 406, 408. The fluid nozzles 578 are maintained a preselected distance Y from the outer layer of the substrate to control the pressure applied to the region 336 by the heated fluid. In some embodiments, the distance Y between the outer layer of the substrate 406 and the fluid nozzles 578 may be maintained within 3 mm of the preselected distance Y. In some embodiments, the distance from the substrate assembly to the fluid nozzles may range from 0 millimeters to about 20 millimeters, or between about 0 millimeters and about 5 millimeters for example, or between about 0.5 millimeters and about 3 millimeters. Control of the distance between the first and second substrate and the fluid orifice may also result in a relatively more predictable fluid spray and melt pattern during the heating process.

A position control apparatus may be used to maintain the absorbent articles within a constant distance from the outer circumferential surface of the drum as the fluid is heating the region. In some embodiments, the position control apparatus 450 may be a belt apparatus 451 as shown in FIG. 7C. The position control apparatus 450 may be located adjacent the bonder apparatus 200 and may take the shape of at least a portion of the support surface 376 and/or the receiving surface 216. The position control apparatus may hold the substrate assembly 190 and/or the chassis 102 in the range of 0 millimeters to about 10 millimeters from the receiving surface 216, or between about 0.5 millimeters to about 5 millimeters from the receiving surface.

In some embodiments, the position control apparatus may be a mechanical apparatus such as clamps or another type of fastener that holds the region 336 of the substrate assembly 190 in place during the bonding process.

The seaming station 548 may also be positioned in a second configuration. In the second configuration, the press member 580 extends through the receiving surface 216, the heating apparatuses 384 are positioned radially inward, and the fluid nozzles 578 are located adjacent to the receiving surface 216. While the member 204 continues to rotate and the seaming station 548 is in the second configuration, the partially melted region 336 approaches the anvil roll 368 located adjacent the receiving surface 216. As the substrate assembly 190 passes between the anvil roll 368 and receiving surface 216, the press member 580, which is extended, compresses the partially melted region against the outer circumferential surface 370 of the anvil roll 368, as illustrated in FIG. 7.

The projections 423 of the press member 580 are configured to contact the same locations of the region that were at least partially melted by the heated fluid, thus forming discrete bond sites 336a in the region. A spring member may be used to apply a predetermined force to the region between the press member 580 and the anvil roll 368. Once compressed, the substrate assembly 190 and chassis 102 advance off of the receiving surface 216. The member continues to rotate and the seaming station shifts back to the first configuration in order to form discrete bond sites in a subsequent substrate assembly.

The heated fluid may include ambient air or other gases. It is to be appreciated that the fluid may be heated to various temperatures and pressurized to various pressures. For example, in some embodiments, the fluid may be heated up to a temperature ranging from the lower melting point of first and second substrates minus 30° C. to the lower melting point of the first and second substrates plus 100° C. In some embodiments, the fluid pressure may range from $0.1 \times 10^5$ Newtons per square meter to $1 \times 10^6$ Newtons per square meter. In some embodiments, the heated fluid may be directed toward at least one of the first and second substrates for a time interval ranging from 10 to 1000 milliseconds or greater. Shorter or greater time intervals may be used.

In some embodiments, the press member may compress the partially melted overlap area against the anvil roll outer circumferential surface at a pressure in the range of about $1 \times 10^5$ Newtons per square meter to about $1 \times 10^8$ Newtons per square meter. In some embodiments, the press member 366 may compress the first and second belt substrates for a time period ranging from 10 to 1000 milliseconds or greater. Shorter or greater time intervals may be used.

The temperature and pressure of the fluid are maintained within a specified range once the nominal set points are selected. For example, a set point may be selected and the temperature may then be maintained in a fixed range around the nominal set point, such as ±30° C., and the pressure may be maintained in a fixed range around the nominal set point, such as ±1 bar. The acceptable range will depend on the relationship between the properties, such as softening point and/or melting temperature, of the materials to be joined and the nominal set point selected.

In some embodiments, the process assembly 220 may include a seaming station 548, such as disclosed in U.S. Patent Publication No. 2013/0218116. The seaming station 548 may use a heated fluid to bond at least a portion of the region 336 of the substrate assembly 190. The fluid may be sufficiently heated to enable at least a partial melting of at least a portion of the substrate assembly 190. A jet of the heated fluid may be directed toward the substrate assembly 190. The fluid may be allowed to penetrate the substrate assembly 190 such that at least a portion of each of the substrate layers is melted in the region, which may be an overlap area 362. The heated fluid, at a controlled temperature and pressure, may pass from the fluid outlet, leading to the formation of controlled and concentrated jets of heated fluid, which are directed toward the region 336 of the substrate assembly 190 to be joined.

By controlled, it is meant that the temperature and pressure are maintained within a specified range once the nominal set points are selected. For example, a set point may be selected from a range, and the temperature may then be maintained in a fixed range around the nominal set point, such as ±30° C., and the pressure may be maintained in a fixed range around the nominal set point, such as ±1 bar. The acceptable range will depend on the relationship between the properties, such as softening point and/or melting temperature, of the materials to be joined and the nominal set point selected. For example, a nominal set point above the melting temperature of one or more of the materials to be joined may require a tighter control range than a nominal set point well below the melting temperature of one or more material to be joined. The control range may be asymmetrical about the nominal set point. By sufficiently heating, it is meant that the fluid is heated to a temperature that will enable at least partial melting, or at least softening, of the substrate or substrates. Sufficient heating may vary with the materials and equipment used. For example, if the heated fluid is applied to the substrate or substrates almost immediately, with little or no time to cool, the fluid may be heated to approximately the softening point or approximately the melting point of the substrate or substrates. If the heated fluid is directed to the substrate or substrates over some gap in time or distance, such that the heated fluid may cool somewhat before interacting with the substrate or substrates, it may be necessary to heat the fluid above, possibly significantly above, the softening point or melting point of the substrate or substrates.

The fluid may also be delivered with a pulsed application. The impact of the jet of heated fluid may be adjusted such that both the energy introduced by the jet plus the energy introduced by other means such as a heated anvil (if the anvil is heated), jet nozzle surface, deformation of the substrate, and the internal friction of substrate layers are sufficient to at least partially melt the meltable components in the region 336 to create a certain tackiness, which will form a strong bond in the region 336, which may include an overlap area 362, upon compression. The melting of the meltable components may occur in a non-uniform manner throughout substrates in the region 336.

The duration of energy transfer in the process described herein may be a dynamic process, and may create a temperature gradient across the cross sections of the meltable components. That is, the core of the meltable components may remain solid while the exterior surface of the meltable components melt or come close to melting. Even below the melting temperature, the exterior surface may reach a softening point, such that plastic deformation of the material may occur at a much lower load than for the same material at ambient temperature. Thus, if one or more of the materials to be bonded have a softening point, the process may be adjusted to achieve a temperature in at least a portion of substrates between the softening point and the melting point. The use of a temperature at or above the softening point but below the melting point of one or more of the meltable components may allow for the creation of a strong bond between the substrate layers with reduced disruption to the structure of the meltable components e.g., attenuating or otherwise weakening the meltable components.

As discussed in more detail below, methods of joining at least two substrate portions may further comprise the step of compressing the region 336 of the substrate assembly 190 with the one or more pressure applying member while the meltable components are at least partially melted, and/or in the tacky state. The temperature of the pressure applying members may be at least below the melting point of the region 336. In some embodiments, the pressure applying member may be heated. The tackiness property of the meltable components permits the joining of substrate layers, which may include a first substrate 406 and a second substrate 408. The pressure applying members may be designed according to aesthetic criteria, for example, to provide discrete, shaped bonds where substrate layers are joined. Discrete bonds may also make the seam easier to open, if desired. The discrete bonds may generally take the shape and spacing of the pressure applying surfaces. As one example, the pressure applying members may be generally oval, or may have any other geometric or decorative shape consistent with the desired removal force and removal force perception. The pressure applying members may be regularly or irregularly spaced, and may be oriented in various directions.

The process assembly 220, as described with reference to FIGS. 7 and 8, may be a seaming station 548. In some embodiments, the seaming station 548 may include a forming block 412 with a pressure applying member 414 extending outwardly from a face 416 of the forming block 412, as illustrated in FIG. 10A. While a single pressure applying member 414 is illustrated, there may be more than one pressure applying member. Adjacent and spaced laterally from the pressure applying member 64 is a fluid outlet 418 including a fluid orifice 420. The fluid outlet 418 may be in fluid communication with a fluid chamber 422 providing a pressurized fluid source for delivery of heated, pressurized fluid to the fluid outlet 418. A heating device 424 may be provided for heating the fluid within the fluid chamber 422. In some embodiments, a valve may control egress of fluid from the fluid chamber 422 and into the fluid outlet 418. As discussed above, a position control member may be used to maintain the substrate assembly 190 within a constant distance from the forming block as the fluid is heating the overlap area. The position control member may hold the substrates in the range of 0 millimeters to about 20 millimeters from the forming block, or between about 0.5 millimeters to about 5 millimeters from the forming block.

Still referring to FIG. 10A, the fluid outlet 418 may be arranged at an angle to vertical, such as for example between about 0 and about 75 degrees; between about 30 and 60 degrees; or about 45 degrees. As such, the fluid outlet 418 directs a jet 426 of heated fluid to a location at least partially beneath the pressure applying member 414 with a pressure applying surface 428 of the pressure applying member 414 spaced away from the substrate assembly 190.

A jet 426 of heated fluid (e.g., air) is directed toward the region 336 of the substrate assembly 190. The jet 426 of heated fluid may distribute in the machine direction MD and cross direction CD as it approaches the substrate assembly 190 forming substantially a cone shape such that the width W at the base of the jet 426 is greater than the diameter of the fluid orifice 420, as illustrated in FIG. 10C. While the jet 426 may be a cone shape, other spray patterns are possible, such as cylindrical, fan-shaped, etc., which may depend, at least in part, on the shape of the fluid orifice 420 and fluid outlet 418, the pressure of the fluid, and type of fluid being used.

The pressure applying member 414 and the fluid orifice 420 may also be separated from each other. For example, the fluid orifice 420 may be offset laterally from the pressure applying member 414. The fluid orifice 420 may be offset from the pressure applying member a distance such that the pressure applying member 414 does not intersect the jet 426. Additionally, the pressure applying surface 428 of the pressure applying member 414 may be spaced away from the substrate assembly 190 during the heating operation. Thus, the pressure applying member 414 does not interfere with the heating of the region 336 of the substrate assembly 190 by the jet 426 of heated fluid.

The forming block 62 may be moving at a constant speed, decreasing speed, increasing speed, or may be stationary while the jet 426 of heated fluid at least partially melts the substrate assembly 190. Once the substrate layers are at least partially melted, the member 204 may rotate the substrate assembly 190 to an anvil roll 368 and the forming block 412 may move toward the substrate assembly 190. Once the member 204 has reached the anvil roll 368, the pressure applying surface 428 of the pressure applying member 414 contacts the region 336 of the substrate assembly 190 at the at least partially melted area. The pressure applying member 414 compresses the region 336 of the substrate assembly 190 together between the pressure applying surface 428 and the anvil roll 368. It is to be appreciated that the anvil roll may alternatively be an anvil block, which traverses linearly to compress the region 336 of the substrate assembly 190.

FIG. 10B illustrates another embodiment of a seaming station 548 for bonding the substrate assembly 190. The traversing seaming apparatus includes a forming block 412. The forming block 412 may include both pressure applying members 414 that extend outwardly from a face 416 of the heating and forming block 412 and fluid outlets 418 that are each in communication with a fluid chamber 422 providing a pressurized fluid source for delivery of heated, pressurized fluid to the fluid outlets 418. A heating device 424 may be provided for heating the fluid within the fluid chamber 422. In some embodiments, valves may control egress of fluid from the fluid chamber 422 and into the fluid outlets 418.

As above, jets of heated fluid are directed toward the substrate assembly 190 at the region 336, which may include an overlap area 362. The region 336 may be maintained a preselected distance from the fluid outlets 418, for example, using a position control device. Once the region 336 is at least partially melted, the forming block 412 may operatively engage the anvil roll 368 thereby compressing the region 336 of the substrate assembly 190.

Although some embodiments have been shown with a fluid outlet located away from and/or apart from the pressure applying member, it is to be appreciated that the fluid outlet may be configured so as to be combined with the pressure applying member. For example, FIG. 10C shows an embodiment with a combination fluid outlet 418 and pressure applying member 414. The pressure applying member 414 includes an outer wall extending outwardly from the face 416 of the forming block 412, an inner wall extending downwardly toward a fluid orifice 420 of the fluid outlet 418 and a pressure applying surface 428 extending between the outer wall and the inner wall.

In some embodiments, the seaming station 548 may be external to the bonder apparatus 200, as illustrated in FIG. 7C. For example, in some embodiments, the seaming station 548 may be positioned adjacent the receiving surface 216 and/or the support surface 202. It is also to be appreciated that in some embodiments, the process assembly 220 may include one of the aforementioned seaming stations 548 and an additional seaming station 548 may be positioned adjacent the receiving surface 216 and/or the support surface 202. In some embodiments, the process assembly 220 may include an anvil block that operatively engages the seaming station 548 positioned adjacent to the receiving surface 216.

Figure 11A:
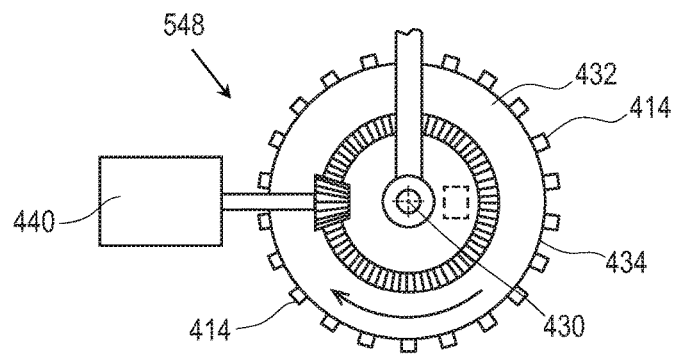
FIG. 11A is a side view of a seaming station in accordance with one non-limiting embodiment of the present disclosure.
Figure 11B:
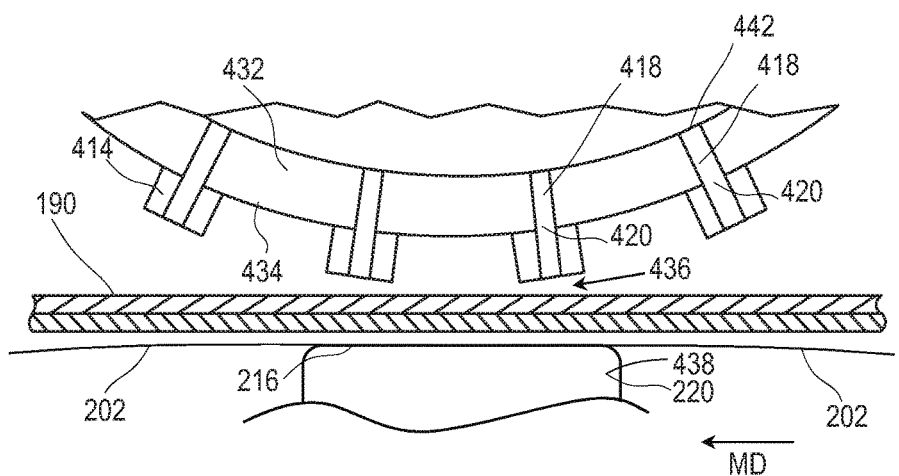
FIG. 11B is a partial side view of a seaming station in accordance with one non-limiting embodiment of the present disclosure.

In some embodiments, the seaming station 548 may be configured as illustrated in FIGS. 11A and 11B. The seaming station 548 may be configured to rotate about an axis of rotation 430 and to bond the region 336 of the substrate assembly 190. The rotary seaming station 548 may be driven by a drive member 440, which may be a motor. The rotary seaming station 548 may include a forming cylinder 432 with pressure applying members 414 extending radially outwardly from an outer circumferential surface 434 of the forming cylinder 432. It is to be appreciated that the forming cylinder 432 may include one or more pressure applying members 414. The pressure applying members 414 may include fluid outlets 418; each fluid outlet 418 may include a fluid orifice 420, as illustrated in FIG. 12B. The fluid outlet 418 may be in fluid communication with a fluid chamber providing a pressurized fluid source for delivery of heated, pressurized fluid, such as air for example, to the fluid outlet 418. In some embodiments, a heating device may be provided for heating the fluid within the fluid chamber. In some embodiments, a valve may control egress of fluid from the fluid chamber and into the fluid outlet 418.

As the member 204 and, more specifically, the receiving surface 216 disposed on the member 204 rotates to the seaming station 548, heated, pressurized fluid may be released from the fluid outlets 418 to heat the region 336 of the substrate assembly 190. The forming cylinder 432 continues to rotate during the release of fluid. The forming cylinder 432 may rotate at substantially the same speed as the member 204. A nip 436 may be formed between the forming cylinder 432 and the process assembly 220. More specifically, each pressure applying member 414 may operatively engage the receiving surface 216 of the process member 220, which may be an anvil block 438. The at least partially melted substrate assembly 190 may be advanced through the nip 436 between the forming cylinder 22 and an anvil block 438. The anvil block 438 may be positioned relative to the forming cylinder 432 such that a pressure applying surface 414 of the pressure applying member 414 may compress the region 336 of the substrate assembly 190, which may include an area of overlap 362, as the substrate assembly 190 advances through the nip 436. In some embodiments, the height of nip 436 may be adjusted to control the pressure applied to the region 336 of the substrate assembly 190. The pressure applied to at least a portion of the region 336 of the substrate assembly 190 may, for example, be in the range of $1 \times 10^5$ Newtons per square meter to $1 \times 10^8$ Newtons per square meter.

Still referring to FIGS. 11A and 11B, the pressure applying member 414 may include, for example, a conical or cylindrical shaped fluid outlet 418 through which the heated fluid may be transferred to at least partially melt the meltable components of the substrate assembly 190. Although the following discussion refers to a cylindrical shaped fluid outlet 418, it is to be appreciated that fluid outlets 418 may have various other shapes, such as for example cones, boxes, and pyramids. A fluid jet nozzle may be connected to the fluid outlet 418. It is to be appreciated that the inlet 442 of the fluid outlet 418 and orifice 420 may be configured to have various different sizes. For example, in some embodiments, the diameter of inlet 442 the cylindrical shaped fluid outlet 418 may range from 1 millimeter to 8 millimeters and the diameter of orifice 420 of cylindrical shaped zone 34 may range from 0.1 millimeters to 6 millimeters.

As previously mentioned, the fluid may include ambient air or other gases. It is to be appreciated that the fluid may be heated to various temperatures and pressurized to various pressures. For example, in some embodiments, the fluid may be heated up to a temperature ranging from the lower melting point of the substrate layers of the substrate assembly 190 minus 30° C. to the lower melting point of the substrate layers of the substrate assembly 190 plus 100° C. In some example configurations, the fluid pressure may range from $0.1 \times 10^5$ Newtons per square meter to $1 \times 10^6$ Newtons per square meter.

In some embodiments, the heated fluid may be directed toward at least a portion of the region 336 of the substrate assembly 190 for a time interval ranging from 10 to 1000 milliseconds or greater. Shorter or greater time intervals may be used. It is to be appreciated that the pressure applying members 414 on the forming cylinder 432 may be disposed in a predetermined pattern, with each pressure applying member 2414 being configured to apply pressure or compress the region 336 of the substrate assembly 190 together after the region 336 have been at least partially melted by the heated fluid.

In addition, there may be a predetermined but adjustable relationship between the surface velocities of the forming cylinder 432 and the member 204. Such a relationship can be synchronous, or asynchronous, that is, with equal surface velocities or with a predetermined surface velocity differential with either the forming cylinder 432 or the member 204 being driven faster than the other.

Similar to the above, in some embodiments, the substrate assembly 190 may be maintained a preselected distance Y from the fluid orifice 420 as the fluid orifice releases the fluid. In some embodiments, the distance Y between the surface of the substrate assembly facing the forming cylinder 432 and the fluid orifice 420 may be between about 0 mm and about 20 mm, such as between about 0 mm and about 5 mm, such as between about 0.5 mm and about 3 mm. The distance Y may be maintained within 3 mm of the preselected distance Y. Control of the distance Y may also result in a relatively more predictable fluid spray and melt pattern during the heating process.

In some embodiments, the process assembly 202 may act on the substrate assembly 190 in processes different than those previously disclosed. For example, the process assembly 202 may include a cutting mechanism, such as with a laser, a knife, or ultrasonic cutting device. The process assembly 202 may be an ultrasonic processes system, such as disclosed in European Patent Application No. 2796271A1.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for forming a bond, the method comprising the steps of:
    advancing a substrate assembly in a machine direction at a first velocity, wherein the substrate assembly comprises a process product pitch defined by a leading portion and a trailing portion, and wherein the substrate assembly comprises a first substrate in facing relationship with a second substrate;
    rotating a bonder apparatus about an axis of rotation at a second velocity, wherein the bonder apparatus comprises a support surface and a process assembly disposed on a portion of the support surface, and wherein the first velocity is greater than the second velocity;
    contracting the substrate assembly, wherein the substrate assembly comprises one or more puckers;
    receiving the leading portion on the process assembly;
    receiving the trailing portion on a subsequent process assembly, wherein the leading portion and the trailing portion define a product arc length, and wherein the product arc length is less than the process product pitch;
    bonding the leading portion and the trailing portion of the substrate assembly;
    removing the substrate assembly from the support surface and the process assembly;
    advancing the substrate assembly through an exit metering assembly such that the substrate assembly exits the metering assembly at the first velocity; and
    expanding the substrate assembly such that the leading portion and the trailing portion are separated by the process product pitch.

2. The method of claim 1, further comprising the step of advancing the substrate assembly through an entry metering assembly, wherein the substrate assembly enters the entry metering assembly at the first velocity.

3. The method of claim 2, wherein the entry metering assembly comprises an entry metering roll configured to rotate about an axis of rotation at the first velocity.

4. The method of claim 1, wherein the exit metering assembly comprises an exit metering roll configured to rotate about an axis of rotation at the first velocity.

5. The method of claim 1, wherein the step of seaming comprises:
    heating a fluid to a temperature sufficient to at least partially melt the first substrate and the second substrate;
    directing a jet of the fluid toward at least one of the leading portion, the trailing portion; and
    partially melting at least a portion of at least one of the leading portion and the trailing portion.

6. The method of claim 1, further comprising compressing at least a portion of the substrate assembly.

7. The method of claim 1, wherein the bonder apparatus further comprises a receiving surface disposed on at least a portion of the process assembly, and wherein the receiving surface defines a fluid aperture, and wherein a jet of heated fluid passes through the fluid aperture toward the substrate assembly.

8. The method of claim 1, wherein the bonder apparatus comprises a receiving surface disposed on at least a portion of the process assembly, and wherein the receiving surface defines a vacuum aperture, and wherein a fluid passes through the vacuum aperture toward the axis of rotation.

9. The method of claim 1, further comprising holding the leading portion and the trailing portion including using a position control member.

10. The method of claim 5, wherein the jet of fluid is expelled from a fluid nozzle, and wherein the fluid nozzle includes a fluid orifice.

11. The method of claim 10, further comprising the step of maintaining the fluid nozzle a distance Y from the outer surface of the substrate assembly, wherein the distance Y from the fluid nozzle to the substrate assembly is in the range of about 0 to about 10 millimeters.

12. The method of claim 5, wherein the jet of heated fluid is at a temperature ranging from a lower melting point of the first and second substrates minus 30° C. to the lower melting point of the first and second substrates plus 100° C.

13. The method of claim 5, wherein the jet of heated fluid is directed at the first and second substrates at a pressure in the range of about $0.1 \times 10^5$ Newtons per square meter to about $1 \times 10^6$ Newtons per square meter, and wherein the jet of heated fluid is directed at the first and second substrates between about 10 milliseconds and about 1000 milliseconds.

14. The method of claim 6, wherein the step of compressing the substrate assembly comprises advancing the substrate assembly between an anvil roll and a bond roll.

15. The method of claim 1, wherein the first substrate and the second substrate are nonwovens.

16. The method of claim 5, wherein the fluid is ambient air.

17. The method of claim 1, further comprising the step of cutting the substrate assembly into individual articles with a knife roll.

18. A method for forming a bond, the method comprising the steps of:
- advancing a substrate assembly in a machine direction at a first velocity, wherein the substrate assembly comprises a process product pitch defined by a leading portion and a trailing portion, and wherein the substrate assembly comprises a first nonwoven substrate, a second nonwoven substrate, and one or more elastic strands between the first substrate and the second substrate;
- moving a bonder apparatus at a second velocity, wherein the bonder apparatus comprises a support surface and a process assembly disposed on a portion of the support surface, and wherein the first velocity is greater than the second velocity;
- advancing the substrate assembly to a first metering roll, wherein the first metering roll is configured to rotate about an axis of rotation at the first velocity;
- contracting the substrate assembly, wherein the substrate assembly comprises one or more puckers;
- receiving the substrate assembly on the bonder apparatus, wherein the leading portion is disposed on the process assembly and the trailing portion is disposed on a subsequent process assembly and the portion of the substrate assembly between the leading portion and the trailing portion is disposed on the support surface;
- advancing the substrate assembly on the bonder apparatus at the second velocity;
- bonding at least a portion of the leading portion and bonding at least a portion of the trailing portion;
- removing the substrate assembly from the support surface and the process assembly;
- advancing the substrate assembly through an exit metering assembly such that the substrate assembly exits the metering assembly at the first velocity; and
- expanding the substrate assembly such that the leading portion and the trailing portion are separated by the process product pitch.

19. The method of claim 18, wherein the leading portion disposed on the process assembly and the trailing portion disposed on the subsequent process assembly defines a product arc length, and wherein the product arc length is less than the process product pitch.

* * * * *